(12) United States Patent
Yanagi et al.

(10) Patent No.: US 6,770,599 B2
(45) Date of Patent: Aug. 3, 2004

(54) TETRAZOLE DERIVATIVES

(75) Inventors: Akihiko Yanagi, Tochigi (JP); Shinichi Narabu, Ibaraki (JP); Toshio Goto, Tochigi (JP); Chieko Ueno, Tochigi (JP); Shinichi Shirakura, Tochigi (JP)

(73) Assignee: Bayer CropScience KK, Tokyo (JP)

( * ) Notice: Subject to any disclaimer, the term of this patent is extended or adjusted under 35 U.S.C. 154(b) by 117 days.

(21) Appl. No.: 10/332,213

(22) PCT Filed: Jun. 25, 2001

(86) PCT No.: PCT/IB01/01130
§ 371 (c)(1),
(2), (4) Date: Feb. 20, 2003

(87) PCT Pub. No.: WO02/02536
PCT Pub. Date: Jan. 10, 2002

(65) Prior Publication Data
US 2003/0224943 A1 Dec. 4, 2003

(30) Foreign Application Priority Data
Jul. 6, 2000 (JP) ........................................ 2000-204914
May 14, 2001 (JP) ........................................ 2001-143072

(51) Int. Cl.$^7$ .......................... A01N 43/713; C07D 57/04
(52) U.S. Cl. ........................................ 504/261; 548/251
(58) Field of Search ........................... 548/251; 504/261

(56) References Cited

U.S. PATENT DOCUMENTS

| 4,885,022 A | 12/1989 | Baba et al. | 71/86 |
| 4,948,887 A | 8/1990 | Baba et al. | 540/603 |
| 4,954,165 A | 9/1990 | Baba et al. | 71/103 |
| 5,094,685 A | 3/1992 | Baba et al. | 71/103 |
| 5,175,299 A | 12/1992 | Baba et al. | 546/248 |
| 5,468,722 A | 11/1995 | Shibata et al. | 504/282 |
| 5,587,484 A | 12/1996 | Shibata et al. | 548/364.4 |
| 5,834,402 A | 11/1998 | Von Deyn et al. | 504/271 |
| 5,846,906 A | 12/1998 | von Deyn et al. | 504/221 |

FOREIGN PATENT DOCUMENTS

| DE | 198 46 792 | 4/2000 | |
| EP | 0 103 143 | 3/1984 | |
| EP | 0 338 992 | 10/1989 | |
| JP | 10-265415 | 10/1998 | |
| JP | 10-265441 | 10/1998 | |
| JP | 11-12275 | 1/1999 | |
| JP | 11-21280 | 1/1999 | |
| WO | 9910327 | * 3/1999 | |

OTHER PUBLICATIONS

Berichte, vol. 28, (month unavailable) 1985, pp. 74–81, Ueber Abkömmlinge des Tetrazoles by Martin Freund and Hans Hempel.

* cited by examiner

Primary Examiner—Robert W. Ramsuer
(74) Attorney, Agent, or Firm—Richard E. L. Henderson; Raymond J. Harmuth

(57) ABSTRACT

The instant invention relates to novel tetrazole derivatives of the formula (I) wherein $R^1$ represents halogen, methyl, ethyl, halomethyl, methoxy, ethoxy, $C_{1-2}$ haloalkoxy, methylthio, ethylthio, $C_{1-3}$ alkylsulfonyl, methylsulfonyloxy, ethylsulfonyloxy, nitro or cyano, $R^2$ represents $C_{1-6}$ alkyl, $C_{3-6}$ cycloalkyl which may be optionally substituted with halogen or $C_{1-3}$ alkyl, $C_{1-4}$ haloalkyl, $C_{2-6}$ alkenyl, or phenyl which may be optionally substituted with halogen, $C_{1-3}$ alkyl, C1-4 haloalkyl, $C_{2-6}$ alkenyl, or phenyl which may be optionally substituted with halogen, $C_{1-3}$ alkyl, $C_{1-2}$ haloalkyl or nitro, m represents 0, 1 or 2, two $R^1$ s may be identical or different, in case m represents 2, n represents 1 or 2, Q represents one the cyclic groups which are mentioned in the specification, to intermediates and several processes for their preparation, to their use as herbicides and to novel compositions containing them.

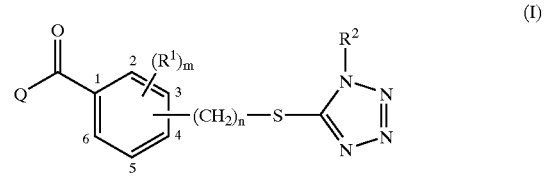

(I)

15 Claims, No Drawings

TETRAZOLE DERIVATIVES

The present invention relates to novel tetrazole derivatives, to processes for their preparation, to their intermediates, to their use as herbicides and to novel herbicidal compositions for use in paddy fields.

It has been already known that certain kinds of tetrazole derivatives show a herbicidal activity (cf. Japanese Laid-open Patent Application No. 12275/1999, No. 21280/1999 etc.). Furthermore, it has been known that certain kinds of heterocyclic derivatives show a herbicidal activity (cf. U.S. Pat. Nos. 5,834,402, 5,846,906, DE-A-19846792, WO 99/10327 etc.).

There have now been found novel tetrazole derivatives of the formula (I)

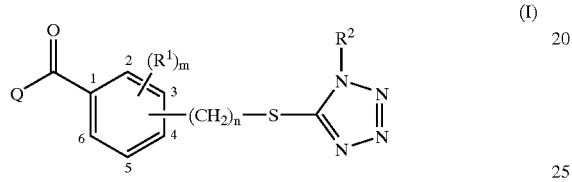

(I)

wherein $R^1$ represents halogen, methyl, ethyl, halomethyl, methoxy, ethoxy, $C_{1-2}$ haloalkoxy, methylthio, ethylthio, $C_{1-3}$ alkylsulfonyl, methylsulfonyloxy, ethylsulfonyloxy, nitro or cyano, $R^2$ represents $C_{1-6}$ alkyl or $C_{3-6}$ cycloalkyl which may be optionally substituted with halogen or $C_{1-3}$ alkyl, or represents $C_{1-4}$ haloallyl, $C_{2-6}$ alkenyl, or phenyl which may be optionally substituted with halogen, $C_{1-3}$ alkyl, $C_{1-2}$ haloalkyl or nitro, m represents 0, 1 or 2, and the two $R^1$ substituents may be identical or different, in case m represents 2, n represents 1 or 2, Q represents one of the following groups

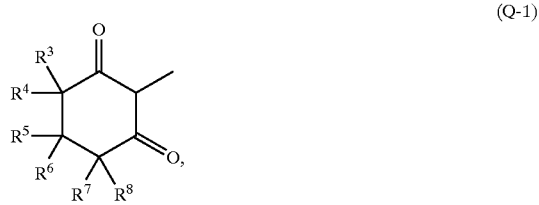
(Q-1)

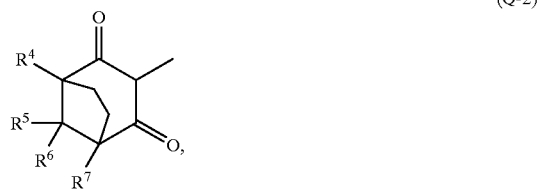
(Q-2)

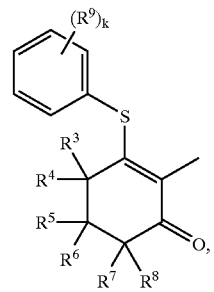
(Q-3)

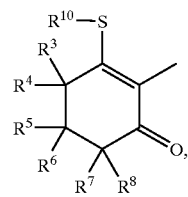
(Q-4)

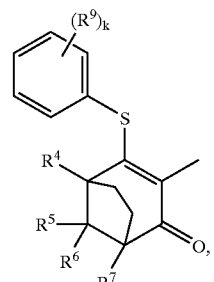
(Q-5)

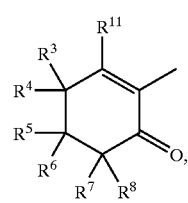
(Q-6)

or (Q-7)

wherein $R^3$, $R^4$, $R^5$, $R^6$, $R^7$ and $R^8$ are identical or different and each represents a hydrogen atom or methyl, $R^9$ represents a hydrogen atom, halogen, $C_{1-3}$ alkyl, halomethyl, methoxy or nitro, $R_{10}$ represents $C_{1-6}$ alkyl, $R^{11}$ represents halogen, and k represents 1 or 2.

The compounds of the formula (I), according to the invention, can be obtained by a process wherein a) in case of preparing a compound of the formula (I) wherein Q represents groups (Q-1) or (Q-2):

compounds of the formula (II)

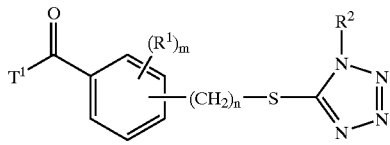

wherein

R¹, R², m and n have the same definition as aforementioned, and

T¹ represents one of the following groups

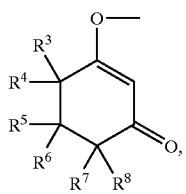

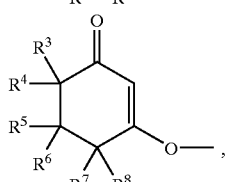

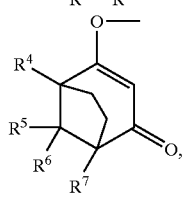

or

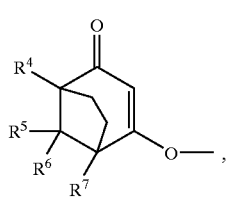

wherein $R^3$, $R^4$, $R^5$, $R^6$, $R^7$ and $R^8$ have the same definition as aforementioned, are reacted to a rearrangement in the presence of inert solvents, and if appropriate, in the presence of a base and a cyanide, and if appropriate, in the presence of a phase-transfer catalyst, or b) in case of preparing a compound of the formula (I) wherein Q represents groups (Q-6) or (Q-7) and $R^{11}$ in said groups represents chloro or bromo:

compounds of the formula (Ib)

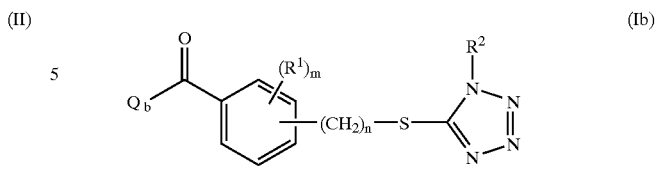

wherein

R¹, R², m and n have the same definition as aforementioned, and $Q_b$ represents one of the following groups

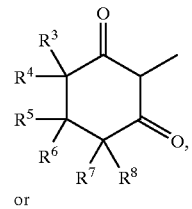

or

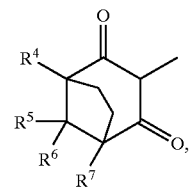

wherein $R^3$, $R^4$, $R^5$, $R^6$, $R^7$ and $R^8$ have the same definition as aforementioned, are reacted with a halogenating agent in the presence of inert solvents, or c) in case of preparing a compound of the formula (I) wherein Q represents groups (Q-3), (Q-4) or (Q-5):

compounds of the formula (Ic)

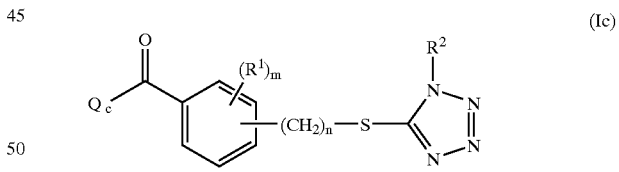

wherein

R¹, R², m and n have the same definition as aforementioned, and $Q_c$ represents one of the following groups

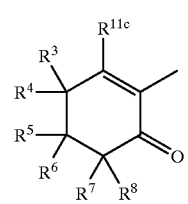

or

-continued

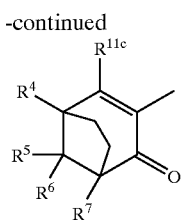

wherein

R³, R⁴, R⁵, R⁶, R⁷ and R⁸ have the same definition as aforementioned, $R^{11c}$ represents chloro or bromo, are reacted with compounds of the formula (III)

      (III)

wherein $R^{12}$ represents the following group

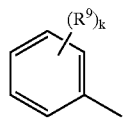

or $R^{10}$ wherein

R⁹, R¹⁰ and k have the same definition as aforementioned, in the presence of inert solvents, and if appropriate, in the presence of an acid binding agent.

The tetrazole derivatives of the formula (I) provided by the present invention show stronger herbicidal activity than with the compounds described in the aforementioned prior art references.

In the formulae:

"Halogen" represents fluoro, chloro, bromo or iodo, and preferably represents fluoro, chloro or bromo.

"Alkyl" can be straight chain or branched chain and there can be specifically mentioned, for example, methyl, ethyl, n- or iso-propyl, n-, iso-, sec- or tert-butyl, n-, iso-, neo-, or tert-pentyl and n- or iso-hexyl.

"Cycloalkyl" includes cyclopropyl, cyclobutyl, cyclopentyl and cyclohexyl. These cycloalkyls may be optionally substituted with halogen (for example, fluoro, chloro, bromo etc.), $C_{1-3}$ alkyl (for example, methyl, ethyl, n- or iso-propyl etc.) and in case that a plurality of substituents exist, they may be identical or different. As specific examples of such substituted cycloalkyls there can be mentioned 1-methylcyclo-propyl, 1-ethylcyclopropyl, 1-n-propylcyclopropyl, 1-methyl-2-fluorocyclopropyl, 2-methylcyclopropyl, 2-fluorocyclopropyl, 1-methyl-2,2-difluorocyclopropyl, 1-methyl-2,2-dichlorocyclopropyl, 2,2difluorocyclopropyl, 2-methylcyclopentyl, 1-methylcyclohexyl, 2-methylcyclohexyl, 3-methylcyclohexyl, 4-methylcyclohexyl, 2,3-dimethylcyclohexyl, 2,6-dimethylcyclohexyl and 2,5-dimethylcyclohexyl.

As "alkenyl" there can be mentioned, for example, vinyl, allyl, 1-methylallyl, 1,1-dimetylallyl and 2-butenyl.

"Haloalkyl" represents straight chain or branched chain alkyl, of which at least one hydrogen is substituted with halogen, and there can be mentioned, for example, $C_{1-4}$ alkyl substituted with 1-6 fluoro and/or chloro, specifically difluoromethyl, trifluoromethyl, 2,2,2-trifluoroethyl, dichloromethyl, 2-chloro-1,1,2-trifluoroethyl, 3-fluoropropyl, 3-chloropropyl, 2,2,3,3,3-pentafluoropropyl and 1,2,2,3,3,3-hexa-fluoropropyl.

The Haloalkyl part in "haloalkoxy" can have the same definition as the afore mentioned "haloalkyl" and as "haloalkoxy" there can be specifically mentioned, for example, difluoromethoxy, trifluoromethoxy, 2-fluoroethoxy, 2-chloroethoxy, 2-bromoethoxy, 2,2,2-trifluoroethoxy and 3-chloropropoxy.

"Alkylsulfonyl" represents an alkyl-$SO_2$-group, wherein the alkyl part has the above-mentioned meaning, and includes specifically methylsulfonyl, ethylsulfonyl, n- or iso-propylsulfonyl.

As preferred definitions in the formula (I) there can be mentioned:

$R^1$ preferably represents fluoro, chloro, bromo, methyl, ethyl, trifluoromethyl, methoxy, ethoxy, $C_{1-2}$ haloalkoxy, methylthio, ethylthio, methylsulfonyl, ethylsulfonyl, methylsulfonyloxy, ethylsulfonyloxy, nitro or cyano.

$R^2$ preferably represents $C_{1-3}$ alkyl, cyclopropyl which may be optionally substituted with fluoro, chloro, methyl or ethyl, $C_{1-3}$ haloalkyl, $C_{2-4}$ alkenyl, or phenyl which may be optionally substituted with fluoro, chloro, methyl, ethyl, trifluoromethyl or nitro.

m preferably represents 1 or 2.

n preferably represents 1 or 2.

$R^9$ preferably represents a hydrogen atom, fluoro, chloro, methyl, ethyl or tri-fluoromethyl.

$R^{10}$ preferably represents methyl or ethyl.

$R^{11}$ preferably represents chloro or bromo.

k preferably represents 1.

As more preferred definitions in the formula (I) there can be mentioned:

$R^1$ more preferably represents chloro, bromo, methyl or methylsulfonyl, $R^2$ more preferably represents methyl, ethyl, n-propyl, isopropyl or cyclopropyl, m more preferably represents 2, and in this case the two $R^1$ substituents are bond respectively to the 2-position and 4-position of a benzene ring and the two $R^1$ substituents may be identical or different.

n more preferably represents represents 1.

In a most preferred group of the inventive compounds the group

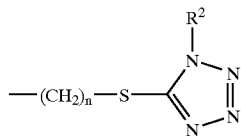

bonds to the 3-position (acccording to formula (I)) of the benzene ring. In another most preferred group Q represents one of the following groups

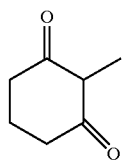

-continued
or

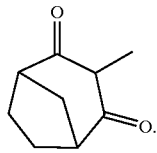

The substituents among the different ranges of preference can be combined without limitation among each other. limitation among each other.

However, as a preferred group of compounds there may be explicitly mentioned the compounds of the formula (I) wherein the substituents have the preferred meaning as described above, and as a more preferred group of compounds there may be explicitly mentioned the compounds of the formula (I) wherein the substituents have the more preferred meaning as described above.

The aforementioned preparation process (a) can be illustrated by the following reaction formula, in case of using, for example, 3-oxo-1-cyclohexenyl 2,4-dichloro-3-{[(1-methyl-1H-tetrazol-5-yl)thio]methyl}benzoate as the starting material.

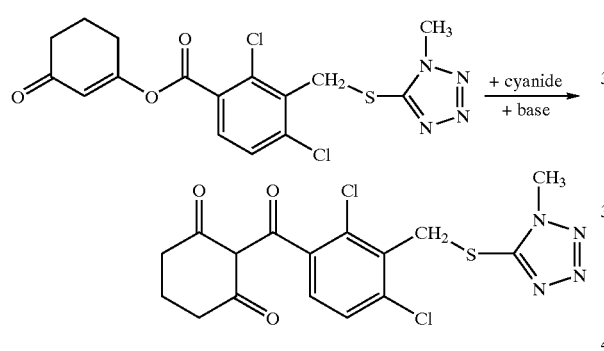

The aforementioned preparation process (b) can be illustrated by the following reaction formula, in case of using, for example, 2-{2,4-dichloro-3-{[(1-methyl-1H-tetrazol-5-yl)thio]methyl}benzoyl}cyclohexane-1,3-dione as the starting material, and, for example, oxalyl dichloride as chlorinating agent.

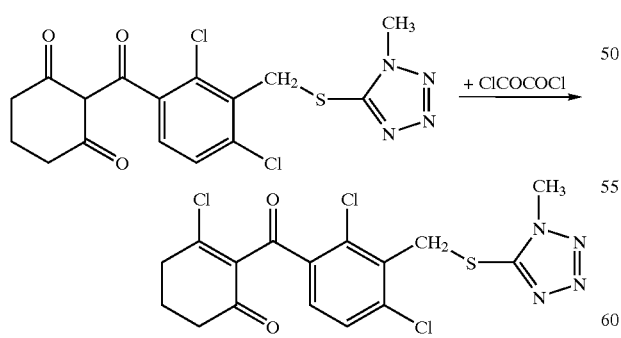

The aforementioned preparation process (c) can be illustrated by the following reaction formula, in case of using, for example, 3-chloro-2-{2,4-dichloro-3-{[(1-methyl-1H-tetrazol-5-yl)thio]methyl}benzoyl}-2-cyclohexen-1-one and thiophenol as the starting materials.

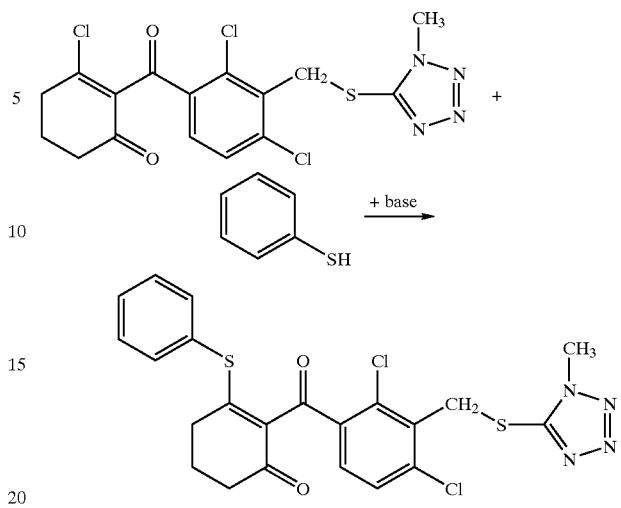

It is further mentioned that the group (Q-1) defined for Q in the above-mentioned formula (I) can also exist in the following two tautomeric forms (Q-1a)

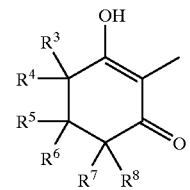

or (Q-1b)

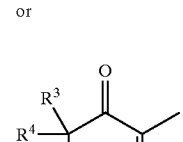

It is also mentioned that the group (Q-2) defined for Q in the above-mentioned formula (I) can also exist in the following two tautomeric forms (Q-2a)

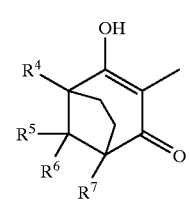

or (Q-2b)

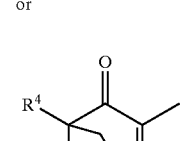

Thus, the compounds of the formula (I) of the present invention include the compounds of the formula (I) wherein Q represents the above-mentioned tautomeric groups (Q-1a), (Q-1b), (Q-2a) or (Q-2b) as group Q-1 or Q-2 respectively. In the present specification, however, it should be understood that these tautomeric groups are represented, unless specified, by the illustration of group (Q-1) or group (Q-2).

The compounds of the formula (II), the starting materials in the above-mentioned preparation process (a), are novel compounds which were not described in the literature up to the present and can be prepared according to the process described in various publications (e.g., Japanese Laid-open Patent Publications No. 222/1990, No. 173/1990, No. 6425/1990 etc.) by reacting compounds of the formula (IV)

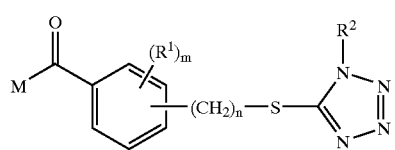
(IV)

wherein $R^1$, $R^2$, m and n have the same definition as aforementioned, and

M represents halogen, with compounds of the formula (V)

 (V)

wherein $Q_a$ represents one of the following groups

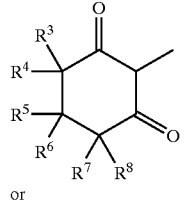 (Q-1)

or

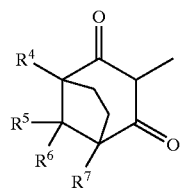 (Q-2)

wherein $R^3$, $R^4$, $R^5$, $R^6$, $R^7$ and $R^8$ have the same definition as aforementioned, in an appropriate diluent, for example, dichloromethane, in the presence of an appropriate condensing agent, for example, triethylamine.

The compounds of the formula (IV) used in the above-mentioned reaction are also novel compounds which were not described in the literature up to the present and can be prepared, for example, by reacting compounds of the formula (VI)

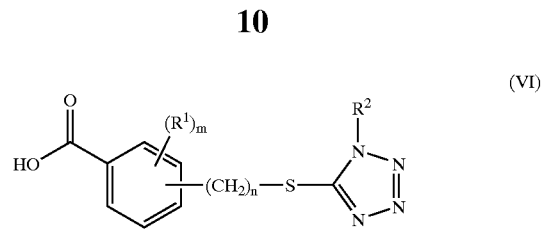
(VI)

wherein $R^1$, $R^2$, m and n have the same definition as aforementioned, with a halogenating agent, for example, phosphorus oxychloride, phosphorus oxy-bromide, phosphorus trichloride, phosphorus tribromide, phosgene, oxalyl dichloride, thionyl chloride, thionyl bromide.

The compounds of the formula (V) used as the starting materials in the preparation of the compounds of the above-mentioned formula (II) are per se known and commercially available or can be easily prepared according to the processes described in various publications (e.g., Japanese Laid-open Patent Publications No. 6425/1990, No. 265415/1998, No. 265441/1998).

The compounds of the formula (VI) used for the preparation of the compounds of the above-mentioned formula (IV) are also novel compounds which were not described in the literature up to the present and can be easily prepared, for example, by hydrolyzing compounds of the formula (VII)

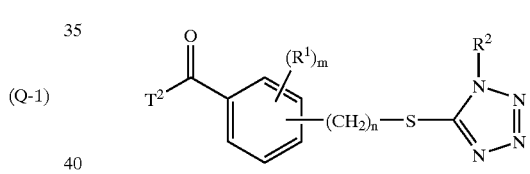
(VII)

wherein $R^1$, $R^2$, m and n have the same definition as aforementioned, and $T^2$ represents $C_{1-4}$ alkoxy, preferably methoxy or ethoxy, in an appropriate diluent, for example, aqueous dioxane, in the presence of an appropriate base, for example, sodium hydroxide.

The compounds of the above-mentioned formula (VII) are also novel compounds and can be easily obtained, for example, by reacting compounds of the formula (VIII)

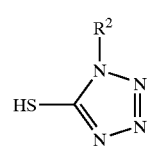
(VIII)

wherein $R^2$ has the same definition as aforementioned with compounds of the formula (IX)

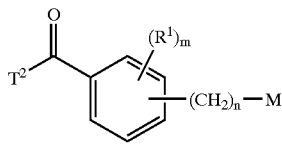
(IX)

wherein
$R^1$, m and n have the same defmition as aforementioned,
$T^2$ represents $C_{1-4}$ alkyl, preferably methyl or ethyl, and
M represents halogen,
in an appropriate diluent, for example, N,N-dimethylformamide, in the presence of an appropriate condensing agent, for example, potassium carbonate.

The compounds of the above-mentioned formula (VIII) are known compounds described, for example, in Berichte Vol. 28, p. 74–76 (1895) and can be easily prepared according to the process described in said publication.

On the other hand, the compounds of the above-mentioned formula (IX), a part of which are novel compounds which were not described in the literature up to the present, can be easily prepared according to the process described, for example, in Japanese Laid-open Patent Publication No. 173/1990.

The compounds of the formula (II), the starting materials in the above-mentioned preparation process (a), can also be easily prepared from compounds of the aforementioned formula (VI) according to the process described, for example, in WO93/18031.

As typical examples of the compounds of the formula (II) used as the starting materials in the aforementioned preparation process (a), the followings can be mentioned:

3-Oxo-1-cyclohexenyl 2-{[(1-methyl-1H-tetrazol-5-yl)thio]methyl}benzoate,
3-oxo-1-cyclohexenyl 2-{[(1-cyclopropyl-1Htetrazol-5-yl)thio]methyl}-4-fluorobenzoate,
3-oxo-1-cyclohexenyl 4-chloro-2-{[(1-methyl-1H-tetrazol-5-yl)thio]methyl}benzoate,
3-oxo-1-cyclohexenyl 4-chloro-2-{[(1-ethyl-1H-tetrazol-5-yl)thio]methyl}benzoate,
3-oxo-1-cyclohexenyl 4-chloro-2-{[(1-cyclopropyl-1H-tetrazol-5-yl)thio]methyl}-benzoate,
3-oxo-1-cyclohexenyl 2-bromo-4-{[(1-methyl-1H-tetrazol-5-yl)thio]methyl}benzoate,
3-oxo-1-cyclohexenyl 4-bromo-2-{[(1-phenyl-1H-tetrazol-5-yl)thio]methyl}benzoate,
3-oxo-1-cyclohexenyl 2-{[(1-methyl-1H-tetrazol-5-yl)thio]methyl}-4-trifluorometh-ylbenzoate,
3-oxo-1-cyclohexenyl 2-{[(1-methyl-1H-tetrazol-5-yl)thio]methyl}-4-methylbenzoate,
3-oxo-1-cyclohexenyl 2,4-dichloro-3-{[(1-methyl-1H-tetrazol-5-yl)thio]methyl}-benzoate,
3-oxo-1-cyclohexenyl 2,4-dichloro-3-{[(1-cyclopropyl-1H-tetrazol-5-yl)thio]meth-yl}benzoate,
3-oxo-1-cyclohexenyl 2,4-dichloro-3-{[(1-(2-chlorophenyl)-1H-tetrazol-5-yl)thio]-methyl}benzoate,
3-oxo-1-cyclohexenyl 2-chloro-3-{[(1-methyl-1H-tetrazol-5-yl)thio]methyl}-4-meth-ylsulfonylbenzoate,
3-oxo-1-cyclohexenyl 2-chloro-3-{[(1-cyclopropyl-1H-tetrazol-5-yl)thio]methyl}-4-methylsulfonylbenzoate,
3-oxo-1-cyclohexenyl 2-chloro-3-{[(1-(n-pentyl)-1H-tetrazol-5-yl)thio]methyl}-4-methylsulfonylbenzoate,
3-oxo-1-cyclohexenyl 2-chloro-3-{[(1-(3-difiuoromethylphenyl)-1H-tetrazol-5-yl)-thio]methyl}-4-methylsulfonylbenzoate,
3-oxo-1-cyclohexenyl 4-chloro-3-{[(1-methyl-1H-tetrazol-5-yl)thio]methyl}-2-meth-ylsulfanylbenzoate,
3-oxo-1-cyclohexenyl 2,4-dimethylsulfanyl-3-{[(1-methyl-1H-tetrazol-5-yl)thio]-methyl}benzoate,
3-oxo-1-cyclohexenyl 4-chloro-3-{[(1-methyl-1H-tetrazol-5-yl)thio]methyl}-2-meth-ylsulfonylbenzoate,
3-oxo-1-cyclohexenyl 2-chloro-4-{[(1-methyl-1H-tetrazol-5-yl)thio]methyl}benzoate,
3-oxo-1-cyclohexenyl 4-{[(1-methyl-1H-tetrazol-5-yl)thio]methyl}-2-methoxybenzo-ate,
3-oxo-1-cyclohexenyl 4-{[(1-methyl-1H-tetrazol-5-yl)thio]methyl}-2-methylsulfon-yloxybenzoate,
3-oxo-1-cyclohexenyl 4-{[(1-methyl-1H-tetrazol-5-yl)thio]methyl}-2-nitrobenzoate,
3-oxo-1-cyclohexenyl 4-{[(1-ethyl-1H-tetrazol-5-yl)thio]methyl}-2-nitrobenzoate,
5,5-dimethyl-3-oxo-1-cyclohexenyl 2-{[(1-methyl-1H-tetrazol-5-yl)thio]methyl}-4-trifluoromethylbenzoate,
4,4-dimethyl-3-oxo-1-cyclohexenyl 2-bromo-4-{[(1-methyl-1H-tetrazol-5-yl)thio]-methyl}benzoate,
4,4-dimethyl-3-oxo-1-cyclohexenyl 2,4-dichloro-3-{[(1-methyl-1H-tetrazol-5-yl)-thio]methyl}benzoate,
4-{4-chloro-2-{[(1-methyl-1H-tetrazol-5-yl)thio]methyl}benzoyloxy}-bicyclo[3.2.1]-3ecten-2-one,
4-{2,4-dichloro-3-{[(1-cyclopropyl-1H-tetrazol-5-yl)thio]methyl}-benzoyloxy}bi-cyclo[3 .2.1]-3-octen-2-one,
4-{2-chloro-3-{[(1-cyclopropyl-1H-tetrazol-5-yl)thio]methyl}-4-methylsulfonyl-benzoyloxy}bicyclo[3.2.1]-3-octen-2-one.

As typical examples of the compounds of the formula (IV) used as the starting materials in the preparation of the compounds of the aforementioned formula (II), the followings can be mentioned:

4-Chloro-2-{[(1-methyl-1H-tetrazol-5-yl)thio]methyl}benzoyl chloride,
4-bromo-2-{[(1-cyclopropyl-1H-tetrazol-5-yl)thio]methyl}benzoyl chloride,
2-{[(1-methyl-1H-tetrazol-5-yl)thio]methyl}-4-trifluoromethylbenzoyl chloride,
2,4-dichloro-3-{[(1-methyl-1H-tetrazol-5-yl)thio]methyl}benzoyl chloride,
2,4-dichloro-3-{[(1-cyclopropyl-1H-tetrazol-5-yl)thio]methyl}benzoyl chloride,
2-chloro-3-{[(1-methyl-1H-tetrazol-5-yl)thio]methyl}-4-methylsulfonyl-benzoyl chloride,
2-chloro-3-{[(1-cyclopropyl-1H-tetrazol-5-yl)thio]methyl}-4-methylsulfonylbenzoyl chloride,
2-chloro-4-{[(1-methyl-1H-tetrazol-5-yl)thio]methyl}benzoyl chloride,
2-bromo-4-{[(1-methyl-1H-tetrazol-5-yl)thio]methyl}benzoyl chloride,
4-{[(1-methyl-1H-tetrazol-5-yl)thio]methyl}-2-nitrobenzoyl chloride,
2,4-dichloro-3-{[(1-methyl-1H-tetrazol-5-yl)thio]methyl}benzoyl bromide,
2-chloro-3-{[(1-methyl-1H-tetrazol-5-yl)thio]methyl}-4-methylsulfonyl-benzoyl bromide, 2-chloro-3-{[(1-cyclopropyl-1H-tetrazol-5-yl)thio]
methyl}-4-methylsulfonylbenzoyl bromide.

As typical examples of the compounds of the formula (VI) used as the starting materials in the preparation of the compounds of the aforementioned formula (IV), the followings can be mentioned:

4-Chloro-2-{[(1-methyl-1H-tetrazol-5-yl)thio]
methyl}benzoic acid,
4-bromo-2-{[(1-cyclopropyl-1H-tetrazol-5-yl)thio]
methyl}benzoic acid,
2-{[(1-methyl-1H-tetrazol-5-yl)thio]methyl}-4-
trifluoromethylbenzoic acid,
2,4-dichloro-3-{[(1-methyl-1H-tetrazol-5-yl)thio]
methyl}benzoic acid,
2,4-dichloro-3-{[(1-cyclopropyl-1H-tetrazol-5-yl)thio]
methyl}benzoic acid,
2-chloro-3-{[(1-methyl-1Htetrazol-5-yl)thio]methyl}-4-
methylsulfonyl-benzoic acid,
2-chloro-3-{[(1-cyclopropyl-1H-tetrazol-5-yl)thio]
methyl}-4-methylsulfonylbenzoic acid,
2-chloro-4-{[(1-methyl-1H-tetrazol-5-yl)thio]
methyl}benzoic acid,
2-bromo-4-{[(1-methyl-1H-tetrazol-5-yl)thio]
methyl}benzoic acid,
4-{[(1-methyl-1H-tetrazol-5-yl)thio]methyl}-2-nitro-
benzoic acid.

As typical examples of the compounds of the formula (VII) used as the starting materials in the preparation of the compounds of the aforementioned formula (VI), the followings can be mentioned.

Methyl 4-chloro-2-{[(1-methyl-1H-tetrazol-5-yl)thio]
methyl}benzoate,
methyl 4-bromo-2-{[(1-cyclopropyl-1H-tetrazol-5-yl)
thio]methyl}-benzoate,
methyl 2-{[(1-methyl-1H-tetrazol-5-yl)thio]methyl}-4-
trifluoromethyl-benzoate,
methyl 2,4-dichloro-3-{[(1-methyl-1H-tetrazol-5-yl)thio]
methyl}-benzoate,
methyl 2,4-dichloro-3-{[(1-cyclopropyl-1H-tetrazol-5-yl)
thio]methyl}-benzoate,
methyl 2-chloro-3-{[(1-methyl-1H-tetrazol-5-yl)thio]
methyl}-4-methylsulfonylbenzoate,
methyl 2-chloro-3-{[(1-cyclopropyl-1H-tetrazol-5-yl)
thio]methyl}-4-methylsulfonyl-benzoate,
methyl 2-chloro-4-{[(1-methyl-1H-tetrazol-5-yl)thio]
methyl}benzoate,
methyl 2-bromo-4-{[(1-methyl-1H-tetrazol-5-yl)thio]
methyl}benzoate,
methyl 4-{[(1-methyl-1H-tetrazol-5-yl)thio]methyl}-2-
nitro-benzoate,
ethyl 2,4-dichloro-3-{[(1-methyl-1H-tetrazol-5-yl)thio]
methyl}benzoate,
ethyl 2-chloro-3-{[(1-methyl-1H-tetrarol-5-yl)thio]
methyl}-4-methylsulfonylbenzoate,
ethyl 2-chloro-3-{[(1-cyclopropyl-1H-tetrazol-5-yl)thio]
methyl}-4-methylsulfonyl-benzoate.

The compounds of the formula (Ib), starting materials in the aforementioned preparation process (b), are a part of the compounds of the formula (a) of the present invention and can be easily prepared according to the above-mentioned preparation process (a).

As typical examples of the compounds of the formula (Ib) used as the starting materials in the aforementioned preparation process (b), the followings, included in the formula (I), can be mentioned:

2-{4-Chloro-2-{[(1-methyl-1H-tetrazol-5-yl)thio]
methyl}benzoyl}-cyclohexane-1,3-dione,
2-{4-bromo-2-{[(1-cyclopropyl-1H-tetrazol-5-yl)thio]
methyl}benzoyl}-cyclohexane-1,3-dione,
2-{2-{[(1-methyl-1H-tetrazol-5-yl)thio]methyl}-4-
trifluoromethyl-benzoyl}cyclo-hexane-1,3-dione,
2-{2,4-dichloro-3-{[(1-methyl-1H-tetrazol-5-yl)thio]
methyl}benzoyl}-cyclohexane-1,3-dione,
2-{2,4-dichloro-3-{[(1-cyclopropyl-1H-tetrazol-5-yl)
thio]methyl}-benzoyl}cyclo-hexane-1,3-dione,
2-{2-chloro-3-{[(1-methyl-1H-tetrazol-5-yl)thio]
methyl}-4-methylsulfonylbenzoyl}cyclohexane-1,3-
dione,
2-{2-chloro-3-{[(1-cyclopropyl-1H-tetrazol-5-yl)thio]
methyl}-4-methylsulfonyl-benzoyl}cyclohexane-1,3-
dione,
2-{2-chloro-4-{[(1-methyl-1H-tetrazol-5-yl)thio]
methyl}benzoyl}-cyclohexane-1,3-dione,
2-{2-bromo-4-{[(1-methyl-1H-tetrazol-5-yl)thio]
methyl}benzoyl}-cyclohexane-1,3-dione,
2-{4-{[(1-methyl-1H-tetrazol-5-yl)thio]methyl}-2-
nitrobenzoyl}-cyclohexane-1,3-dione,
3-{2-chloro-3-{[(1-cyclopropyl-1H-tetrazol-5-yl)thio]
methyl}-4-methylsulfonyl-benzoyl}bicyclo[3.2.1]-
octane-2,4-dione As a halogenating agent used for the reaction with the compounds of the formula (Ib) in the preparation process (b) there can be mentioned, for example, thionyl chloride, thionyl bromide, oxalyl dichloride, oxalyl dibromide etc.

The compounds of the formula (Ic), the starting materials in the aforementioned preparation process (c), are a part of the compounds of the formula (I) of the present invention and can be easily prepared according to the above-mentioned preparation process (b).

As typical examples of the compounds of the formula (Ic) used as the starting materials in the aforementioned preparation process (c), the followings, included in the formula (I), can be mentioned:

3-Chloro-2-{4-chloro-2-{[(1-methyl-1H-tetrazol-5-yl)
thio]methyl}-benzoyl}-2-cyclohexen-1-one,
3-chloro-2-{4-bromo-2-{[(1-cyclopropyl-1H-tetrazol-5-
yl)thio]methyl}-benzoyl}-2-cyclohexen-1-one,
3-chloro-2-{2-{[(1-methyl-1H-tetrazol-5-yl)thio]
methyl}-4-trifluoromethylbenzoyl}-2-cyclohexen-1-
one,
3-chloro-2-{2,4-dichloro-3-{[(1-methyl-1H-tetrazol-5-
yl)thio]methyl}-benzoyl}-2-cyclohexen-1-one,
3-chloro-2-{2,4-dichloro-3-{[(1-cyclopropyl-1H-
tetrazol-5-yl)thio]methyl}benzoyl}-2-cyclohexen-1-
one,
3-chloro-2-{2-chloro-3-{[(1-methyl-1H-tetrazol-5-yl)
thio]methyl}-4-methylsulfonyl-benzoyl}-2-
cyclohexen-1-one,
3-chloro-2-{2-chloro-3-{[(1-cyclopropyl-1H-tetrazol-5-
yl)thio]methyl}-4-methylsulfonylbenzoyl}-2-
cyclohexen-1-one,
3-chloro-2-{2-chloro-4-{[(1-methyl-1H-tetrazol-5-yl)
thio]methyl}-benzoyl}-2-hexen-1-one,
3-chloro-2-{2-bromo-4-{[(1-methyl-1H-tetrazol-5-yl)
thio]methyl}-benzoyl}-2-cyclohexen-1-one,
3-chloro-2-{4-{[(1-methyl-1H-tetrazol-5-yl)thio]
methyl}-2-nitrobenzoyl}-2-cyclohexen-1-one, 4-chloro-2-{2-chloro-3-{[(1-cyclopropyl-1H-tetrazol-5-yl)thio]methyl}4-methyl-sulfonylbenzoyl}bicyclo[3.2.1]-3-octen-2-one.

The compounds of the formula (III), the starting materials in the above-mentioned preparation process (c), are thiol compounds well known in the field of organic chemistry and as typical examples of the compounds of the formula (III) the followings can be mentioned:

Methyl mercaptan,
ethyl mercaptan,
thiophenol,
4-fluorothiophenol,
4-chlorothiophenol,
2-methylthiophenol,
4-ethylthiophenol,
4-triflubromethylthiophenol etc.

Each compound of the formulae (II), (V), (VI) and (VII), starting material or intermediate product in the aforementioned processes (a)–(c) for the preparation of the compounds of the formula (I) of the present invention is a novel compound which was not described in the literature up to the present. The compounds can be illustrated collectively by the following general formula (X)

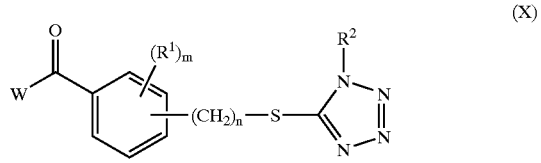

wherein
W represents $T^1$, hydroxy or $T^2$, wherein
$R^1$, $R^2$, m, n, $T^1$, $T^2$ and M have the same definition as aforementioned.

The reaction of the aforementioned preparation process (a) can be conducted in an appropriate diluent. As examples of such diluents there can be mentioned aliphatic, alicyclic and aromatic hydrocarbons (which may optionally be chlorinated), for example, toluene, dichloromethane, chloroform and 1,2-dichloroethane; ethers, for example, ethyl ether, dimethoxyethane (DME) and tetrahydrofuran (THF); ketones, for example, methyl isobutyl ketone (MIBK); nitrites, for example, acetonitrile; esters, for example, ethyl acetate; acid amides, for example, dimethylformamide (DMF).

The preparation process (a) can be conducted in the presence of a cyanide and a base. As a cyanide usable in that case there can be mentioned, for example, sodium cyanide, potassium cyanide, acetone cyanohydrin and hydrogen cyanide. As a base there can be mentioned, for example, as inorganic bases, hydroxides and carbonates of alkali metals and alkaline earth metals, for example, sodium carbonate, potassium carbonate, lithium hydroxide, sodium hydroxide, potassium hydroxide and calcium hydroxide; and as organic bases, tertiary amines, dialkylaminoanilines and pyridines, for example, triethylamine, pyridine, 4-dimethylaminopyridine (DMAP), 1,4-diazabicyclo[2,2,2]octane (DABCO) and 1,8-diazabicyclo[5,4,0]undec-7-ene (DBU).

The aforementioned preparation process (a) can be conducted also in the co-existence of a phase-transfer catalyst. As examples of the phase-transfer catalyst usable in that case there can be mentioned crown ethers, for example, dibenzo-18-crown-6, 18-crown-6 and 15-crown-5.

The reaction of the preparation process (a) can be conducted in a substantially wide range of temperatures. Suitable temperatures are in the range of generally about −10 to about 80° C., preferably about 5 to about 40° C. Said reaction is conducted desirably under normal pressure. Optionally, however, it is possible to conduct it under elevated pressure or under reduced pressure.

In conducting the preparation process (a) the target compounds of the afore mentioned formula (I), in case that Q represents groups (Q-1) or (Q-2), can be obtained, for example, by reacting 1 mole of a compound of the formula (II) with 1 to 4 moles of triethylamine in a dildent, for example, acetonitrile, in the presence of 0.01 to 0.5 moles of acetone cyanohydrin.

In conducting the preparation process (a) it is possible to obtain the compounds of the formula (I) by conducting reactions starting from the compounds of the aforementioned formula (VI) continuously in one pot without isolating the compounds of the formulae (IV) and (II).

The reaction of the aforementioned preparation process (b) can be conducted in an appropriate diluent. As examples of such there can be mentioned aliphatic, alicyclic and aromatic hydrocarbons (which may optionally be chlorinated), for example, pentane, hexane, cyclohexane, petroleum ether, ligroine, benzene, toluene, xylene, dichloromethane, chloroform, carbon tetrachloride, 1,2-dichloroethane and chloro-benzene; ethers, for example, ethyl ether, methyl ethyl ether, isopropyl ether, butyl ether, dioxane, dimethoxyethane (DME), tetrahydrofuran (THF) and diethylene glycol dimethyl ether (DGM); ketones, for example, acetone, methyl ethyl ketone (MEK), methyl isopropyl ketone and methyl isobutyl ketone (MEBK); nitrites, for example, acetonitrile and propionitrile; esters, for example, ethyl acetate and amyl acetate; acid amides, for example, dimethylformamide (DMF), dimethylacetamide (DMA), N-methylpyrrolidone, 1,3-dimethyl-2-imidazolidinone and hexamethyl-phosphoric triamide (HMPA).

The reaction of the preparation process (b) can be conducted in a substantially wide range of temperatures. Suitable temperatures are in the range of generally about −20 to about 100°C., preferably about 0 to about 50° C. Said reaction is conducted desirably under normal pressure. Optionally, however, it is possible to conduct it under elevated pressure or under reduced pressure.

In conducting the preparation process (b) the target compounds of the afore mentioned formula (I), in case that Q represents groups (Q-6) or (Q-7), wherein $R^{11}$ in said group represents chloro or bromo, can be obtained, for example, by reacting 1 mole of a compound of the formula (Ib) with 1 to 5 moles of oxalyl dichloride in a diluent, for example, dichloromethane.

The reaction of the aforementioned preparation process (c) can be conducted in an appropriate diluent. As examples of such diluents there can be mentioned aliphatic, alicyclic and aromatic hydrocarbons (which may optionally be chlorinated), for example, pentane, hexane, cyclohexane, petroleum ether, ligroine, benzene, toluene, xylene, dichloromethane, chloroform, carbon tetrachloride, 1,2-dichloroethane, chlorobenzene and dichlorobenzene; ethers, for example, ethyl ether, methyl ethyl ether, isopropyl ether, butyl ether, dioxane, dimethoxyethane (DME), tetrahydrofuran (THF) and diethylene glycol dimethyl ether (DGM); ketones, for example, acetone, methyl ethyl ketone (MEK), methyl isopropyl ketone and methyl isobutyl ketone (MIBK); nitriles, for example, acetonitrile, propionitrile and acrylonitrile; esters, for example, ethyl acetate and amyl acetate; acid amides, for example, dimethyl-formamide (DMF), dimethylacetamide (DMA) and N-methylpyrrolidone; sulfones and sulfoxides, for example, dimethyl sulfoxide (DMSO) and sulfolane; bases, for example, pyridine.

The preparation process (c) can be conducted in the presence of a condensing agent. As a usable condensing agent there can be for example mentioned, as inorganic bases, hydrides and carbonates of alkali metals, for example, sodium hydride, lithium hydride, sodium carbonate and potassium carbonate; and as organic bases, tertiary amines, dialkylaminoanilines and pyridines, for example, triethylamine, 1,1,4,4-tetramethylethylenediarnine (TMEDA), pyridine, 4-dimethylaminopyridine (DMAP), 1,4-diazabicyclo[2,2,2]octane (DABCO) and 1,8-iazabicyclo[5,4,0]undec-7-ene (DBU).

The reaction of the preparation process (c) can be conducted in a substantially wide range of temperatures. Suitable temperatures are in the range of generally about −20 to about 140° C., preferably about 0 to about 100° C. Said reaction is conducted desirably under normal pressure. Optionally, however, it is possible to conduct it under elevated pressure or under reduced pressure.

In conducting the preparation process (c) the target compounds of the afore-mentioned formula (I), in case that Q represents groups (Q-3), (Q-4) or (Q-5) can be obtained, for example, by reacting 1 mole of a compound of the formula (Ic) with 1 to 5 moles of thiophenol in a diluent, for example, tetrahydrofuran in the presence of 1 to 5 moles of triethylamine.

The active compounds of the aforementioned formula (I), according to the present invention, show, as shown in the biological test examples to be described later, excellent herbicidal activities against various weeds and can be used as herbicides. In the present specification weeds mean, in the broadest sense, all plants which grow in locations where they are undesired. The compounds, according to the present invention, act as total or selective herbicides depending upon the applied concentration. The active compounds, according to the present invention, can be used, for example, between the following weeds and cultures.

Dicotyledon weeds of the genera: Sinapis, Lepidium, Galium, Stellaria, Cheno-podium, Urtica, Senecio, Amaranthus, Portulaca, Xanthium, Ipomoea, Polygonum, Ambrosia, Cirsium, Sonchus, Solanum, Rorippa, Lamium, Veronica, Datura, Viola, Galeopsis, Papaver, Centaurea, Galinsoga, Rotala, Lindernia etc.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita etc.

Monocotyledon weeds of the genera: Echinochloa, Setaria, Panicum, Digitaria, Phleum, Poa, Festuca, Eleusine, Lolium, Bromus, Avena, Cyperus, Sorghum, Agropyron, Monochoria, Fimbristylis, Sagittaria, Eleocharis, Scirpus, Paspalum, Ischaemum, Agrostis, Alopecurus, Cynodon etc.

Monocotyledon cultures of the genera: Oryza, Zea, Triticum, Hordeum, Avena, Secale, Sorghum, Panicum, Saccharum, Ananas, Asparagus, Allium etc.

The use of the compounds, according to the present invention, is not restricted to the above-mentioned plants, but may be applied to other plants in the same manner. The active compounds, according to the present invention, can, depending upon the applied concentration, non-selectively control weeds and can be used, for example, on industrial terrain, rail tracks, paths, places with or without tree plantings. Moreover, the active compounds, according to the present invention, can be used for controlling weeds in perennial cultures and applied in, for example, afforestations, decorative tree plantings, orchards, vineyards, citrus groves, nut orchards, banana plantations, coffee plantations, tea plantations, rubber plantations, oil palm plantations, cocoa plantations, soft fruit plantings, hopfields etc. and can be applied also for the selective controlling of weeds in annual cultures.

According to the invention all plants and plant parts can be treated. The term plants includes all plants and plant populations, such as desired or undesired wild plants and cultivated plants (including naturally occurring cultivated varieties). Cultivated plants can be plant varieties that were obtained by conventional breeding and optimizing processes or by biotechnological and genetic engineering methods or a combination of such processes and methods, including transgenic plants and including plant varieties that cannot or can be protected by plant patents or plant variety rights. Plant parts are all parts and organs of plants occurring above or below the surface of the soil, e.g. shoots, leaves, needles, stalks and stems, trunks, flowers, fruits and seeds as well as roots, tubers, bulbs and rhizomes. The term plant parts also includes harvested crops and propagation material, e.g. cuttings, tubers, bulbs, rhizomes, shoots and seeds.

According to the invention the plants and plant parts are treated using the usual methods by applying the active ingredients or compositions containing them directly to the plants or plant parts or to their surroundings (including the soil) or storeroom, e.g. by dipping, spraying, dusting, fogging, spreading and in the case of propagation material also by coating using one or multiple layers.

The active compounds, according to the present invention, can be made into the customary formulations. As such formulations there can be mentioned, for example, solutions, wettable powders, emulsions, suspensions, powders, water-dispersible granules, tablets, granules, suspension-emulsion concentrates, microcapsules in polymeric substances, jumbo formulations etc.

These formulations can be prepared according to per se known methods, for example, by mixing the active compounds with extenders, namely liquid or solid diluents or carriers, and optionally with surface-active agents, namely emulsifiers and/or dispersants and/or foam-forming agents.

As liquid diluents or carriers there can be mentioned, for example, aromatic hydro-carbons (for example, xylene, toluene, alkylnaphthalene etc.), chlorinated aromatic or chlorinated aliphatic hydrocarbons (for example, chlorobenzenes, ethylene chlorides, methylene chloride etc.), aliphatic hydrocarbons [for example, cyclohexane etc. or paraffins (for example, mineral oil fractions etc.)], alcohols (for example, butanol, glycol etc.) and their ethers, esters etc., ketones (for example, acetone, methyl ethyl ketone, methyl isobutyl ketone, cyclohexanone etc.), strongly polar solvents (for example, dimethylformamide, dimethyl sulphoxide etc.) and water. In case of using water as extender, for example, organic solvents can be used as auxiliary solvents.

As solid diluents or carriers there can be mentioned, for example, ground natural minerals (for example, kaolin, clay, talc, chalk, quartz, attapulgite, montmorillonite, diatomaceous earth etc.), ground synthetic minerals (for example, highly dispersed silicic acid, alumina, silicates etc.) etc. As solid carriers for granules there can be mentioned, crushed and fractionated rocks (for example, calcite, marble, pumice, sepiolite, dolomite etc.), synthetic granules of inorganic and organic meals, particles of organic materials (for example, sawdust, coconut shells, maize cobs and tobacco stalks etc.) etc.

As emulsifiers and/or foam-forming agents there can be mentioned, for example, nonionic and anionic emulsifiers

[for example, polyoxyethylene fatty acid esters, polyoxyethylene fatty acid alcohol ethers (for example, alkylaryl polyglycol ethers, alkylsulphonates, alkylsulphates, arylsulphonates etc.)], albumin hydrolysis products etc.

Dispersants include, for example, ligninsulphite waste liquor, methyl cellulose etc.

Tackifiers can also be used in formulations (powders, granules, emulsions). As said tackifiers there can be mentioned, for example, carboxymethyl cellulose, natural and synthetic polymers (for example, gum arabic, polyvinyl alcohol, polyvinyl acetate etc.).

Colorants can also be used. As said colorants there can be mentioned inorganic pigments (for example, iron oxide, titanium oxide, Prussian Blue etc.) and organic dyestuffs such as alizarin dyestuffs, azo dyestuffs or metal phthalocyanine dyestuffs, and further trace nutrients such as salts of metals such as iron, manganese, boron, copper, cobalt, molybdenum, zinc etc.

Said formulations can contain the active compounds of the formula (I) in a range of generally 0.1 to 95 % by weight, preferably 0.5 to 90 % by weight.

The active compounds of the formula (I), according to the present invention, can be used as such or in their formulation forms for controlling weeds. They can be used also as a mixed agent with known herbicides. Such a mixed agent can be previously prepared as a final formulation form or can be prepared by tank-mixing on occasion of application. As herbicides usable in combination with the compounds of the formula (I), according to the present invention, as a mixed agent there can be specifically mentioned, for example, the following herbicides shown in common names.

Acetamnide type herbicides, for example, pretilachlor, butachlor, tenylchlor, alachlor etc.;

amide type herbicides, for example, clomeprop, etobenzanid etc.;

benzofuran type herbicides, for example, benfuresate etc.;

indanedione type herbicides, for example, indanofan etc.;

pyrazole type herbicides, for example, pyrazolate, benzofenap, pyrazoxyfen etc.;

oxazinone type herbicides, for example, oxaziclomefone etc.;

sulfonylurea type herbicides, for example, bensulfuron-methyl, azimsulfuron, imazosulfuron, pyrazosulfuron-ethyl, cyclosulfamron Ethoxysulfuron, Halosulfuiron (-methyl) etc.;

thiocarbamate type herbicides, for example, thiobencarb, molinate, pyributycarb etc.;

triazine type herbicides, for example, dimethametryn Simetryn etc.;

triazole type herbicides, for example, cafenstrole etc.;

quinoline type herbicides, for example, quinclorac etc.;

isoxazole type herbicides, for example, isoxaflutole etc.;

dithiophosphate type herbicides, for example, anilofos etc.;

oxyacetamide type herbicides, for example, mefenacet, flufenacet etc.;

tetrazolinone type herbicides, for example, fentrazamide etc.;

dicarboxyimide type herbicides, for example, pentoxazone etc.;

trione type herbicides, for example, sulcotrione, benzobicyclon etc.;

phenoxypropinate type herbicides, for example, cyhalofop-butyl etc.;

benzoic acid type herbicides, for example, pyriminobac-methyl etc.;

diphenylether type herbicides, for example, chlomethoxyfen, oxyfluorfen etc.;

pyridinedicarbothioate type herbicides, for example, dithiopyr etc.;

phenoxy type herbicides, for example, MCPA, MCPB etc.;

urea type herbicides, for example, dymron, cumyluron etc.;

naphthalenedione type herbicides, for example, quinoclamine etc.;

isoxazolidinone type herbicides, for example, clomazone etc.

diphenylether type herbicides, for example, chlomethoxyfen, oxyfluorfen etc.;

pyridinedicarbothioate type herbicides, for example, dithiopyr etc.;

phenoxy type herbicides, for example, MCPA, MCPB etc.;

urea type herbicides, for example, dymron, cumyluron etc.;

naphthalenedione type herbicides, for example, quinoclamine etc.;

isoxazolidinone type herbicides, for example, clomazone etc.

In addition to the above mentioned herbicides, the following herbicides, shown in common names, for example, Acetochlor, Acifluorfen (-sodium), Aclonifen, Alloxydirn (-sodium), Ainetryne, Amicarbazone, Amidochlor, Amidosulfuron, Arnitrole, Asulam, Atrazine, Azafenidin, Beflubutamid, Benazolin (-ethyl), Bentazon, Benzfendizone, Benzoylprop (-ethyl), Bialaphos, Bifenox, Bispyribac -(sodium), Bromacil, Bromobutide, Bromofenoxim, Bromoxynil, Butafenacil -(allyl), Butenachlor, Butralin, Butroxydim, Butylate, Carbetamide, Carfentrazone (-ethyl), Chloramben, Chloridazon, Chlorimuron (-ethyl), Chlornitrofen, Chlorsulfuron, Chlorthiarnid, Chlortoluron, Cinidon (-ethyl), Cinmethylin, Cinosuffiron, Clefoxydim, Clethodim, Clodinafop (-propargyl), Clopyralid, Cloransulam (-methyl), Cyanazine, Cybutryne, Cycloate, Cycloxydim, 2,4-D, 2,4-DB, Desmedipham, Diallate, Dicamba, Dichlobenil, Dichlorprop (-P), Diclofop (-methyl), Diclosulam, Diethatyl (-ethyl), Difenopenten (-ethyl), Difenzoquat, Diflufenican, Diflufenzopyr, Dikegulac (-sodium), Dimefuron, Dimepiperate, Dimethachlor, Dimethenamid (-P), Dimexyflam, Dinitramine, Diphenamid, Diquat (-dibromide), Diuron, Epropodan, EPTC, Esprocarb, Ethalfluralin, Ethametsulfuron (-methyl), Ethiozin, Ethofumesate, Ethoxyfen, Fenoxaprop (-P-ethyl), Flamprop (-M-isopropyl, -M-methyl), Flazasuilron, Florasulam, Fluazifop (-P-butyl), Fluazolate, Flucarbazone (-sodium), Fluchloralin, Flumetsulam, Flumiclorac (-pentyl), Flumioxazin, Flumipropyn, Fluometuron, Fluorochloridone, Fluoroglycofen (-ethyl), Flupoxam, Flupropacil, Flurpyrsulfuron (-methyl, -sodium), Flurenol (-butyl), Fluridone, Fluroxypyr (-butoxypropyl, -meptyl), Flurprimidol, Flurtamone, Fluthiacet (-methyl), Fomesafen, Foramsulfuron, Glufosinate (-ammonium), Glyphosate (-ammonium, -isopropylammonium), Halosafen, Haloxyfop (-ethoxyethyl, -P-methyl), Hexazinone, Imazamethabenz (-methyl), Imazamethapyr, Imaza-mox, Imazapic, Imazapyr, Imazaquin, Imazethapyr, Iodosulfuron (-methyl, -sodium), Ioxynil, Isopropalin, Isoproturon, Isouron, Isoxaben, Isoxachlortole, Isoxadifen (-ethyl), Isoxapyrifop, Ketospiradox, Lactofen, Lenacil, Linuron, Mecoprop (-P), Mesotrione, Metamitron, Metazachlor, Methabenzthiazuron, Methyldymron, Metobenzuron, Metobromuron, (S-) Metolachlor, Metosulam, Metoxuron, Metribuzin, Metsulfuron (-methyl), Monolinuron, Naproanilide, Napropamide, Neburon, Nicosulfliron, Norflurazon, Orbencarb, Oryzalin, Oxadiargyl, Oxadiazon, Oxasulfuron, Paraquat, Pelargonsaure, Pendimethalin, Pendralin, Pethoxamid, Phenmedipham, Picolinafen, Piperophos, Primisulfuiron (-methyl), Profluazol, Profoxydim, Prometryn, Propachlor, Propanil, Propaquizafop, Propisochlor, Propoxycarbazone (-sodium), Propyzamide, Prosulfocarb, Prosulfuron, Pyraflufen (-ethyl), Pyrazogyl, Pyribenzoxim, Pyridafol, Pyridate, Pyridatol, Pyriftalid, Pyrithiobac (-sodium), Quinmerac, Quizalofop (-P-ethyl, -P-tefuryl), Rimsulfiron, Sethoxydim, Simazine, Sulfentrazone, Sulfometuron (-methyl), Sulfosate, Sulfosulfuron, Tebutam, Tebuthiuron, Tepraloxydim, Terbuthylazine, Terbutryn, Thiazopyr, Thidiazimin, Thifensuifiron (-methyl), Tiocarbazil, Tralkoxydim, Triallate, Triasulfuron, Tribenuron (-methyl), Triclopyr, Tnidiphane, Trifloxy-sulfuron, Trifluralin, Triflusuulfuron (-methyl), Tritosulfiuron.

The above-mentioned herbicides are known herbicides mentioned in "Pesticide Manual" 2000, published by The British Crop Protect Council.

The weight ratios of the groups of active substances in the mixed compositions can vary within relatively wide ranges.

For instance, per part by weight of (1) the compounds of the formula (I), 0.2 to 14 parts by weight of acetamide type herbicides, preferably 0.66 to 5 parts by weight;

2 to 40 parts by weight of amide type herbicides, preferably 3.96 to 16 parts by weight;

0.2 to 20 parts by weight of benzofuran type herbicides, preferably 1.00 to 6 parts by weight;

0.2 to 8 parts by weight of indanedione type herbicides, preferably 0.49 to 2 parts by weight;

0.06 to 4 parts by weight of oxazinone type herbicides, preferably 0.20 to 0.8 parts by weight;

0.02 to 4 parts by weight of sulfonylurea type herbicides, preferably 0.07 to 1.2 parts by weight;

1 to 100 parts by weight of thiocarbamate type herbicides, preferably 2.47 to 40 parts by weight;

0.6 to 12 parts by weight of triazine type herbicides, preferably 1.32 to 4.5 parts by weight;

0.1 to 8 parts by weight of triazole type herbicides, preferably 0.33 to 3 parts by weight;

0.2 to 10 parts by weight of dithiophosphate type herbicides, preferably 1.00 to 4 parts by weight;

0.2 to 50 parts by weight of oxyacetamide type herbicides, preferably 1.00 to 12 parts by weight;

0.02 to 10 parts by weight of tetrazolinone type herbicides, preferably 0.17 to 3 parts by weight;

0.1 to 12 parts by weight of dicarboxyimide type herbicides, preferably 0.33 to 4.5 parts by weight;

0.2 to 12 parts by weight of phenoxypropinate type herbicides, preferably 0.4 to 1.8 parts by weight;

0.6 to 20 parts by weight of diphenylether type herbicides, preferably 1.65 to 7.5 parts by weight;

0.02 to 14 parts by weight of pyridinedicarbotlioate type herbicides, preferably 0.20 to 5 parts by weight;

0.2 to 10 parts by weight of phenoxy type herbicides, preferably 0.66 to 4 parts by weight, and 2 to 80 parts by weight of urea type herbicides, preferably 4.95 to 25 parts by weight, are used.

Furthermore, the active compounds of the formula (I) according to the present invention, can be mixed also with a safener and their application as a selective herbicide can be broadened to reduce phytotoxicity and to provide wider weed-control spectrur by such a mixing.

As an example of the safener, the following safeners can be mentioned; AD-67, BAS-145138, Benoxacor, Cloquintocet (-mexyl), Cyometrinil, 2,4-D, DKA-24, Dichlormid, Dymron, Fenclorim, Fenchlorazol (-ethyl), Flurazole, Fluxofenim, Furilazole, Isoxadifen (-ethyl), MCPA, Mecoprop (-P), Mefenpyr (-diethyl), MG-191, Naphthalic anhydride, Oxabetrinil, PPG-1292, R-29148.

The above-mentioned safeners are known safeners mentioned in "Pesticide Manual", 2000, published by The British Crop Protect Council.

The weight ratios of the groups of active substances in the mixed comositions can vary within relatively wide ranges.

For instance, per part by weight of (1) the compounds of the formula (I), 0.05 to 50 parts by weight of Dichlormid, preferably 0.1 to 10 parts by weight;

0.05 to 50 parts by weight of Dymron, preferably 0.1 to 10 parts by weight;

0.05 to 50 parts by weight of Fenclorim, preferably 0.1 to 10 parts by weight;

0.05 to 50 parts by weight of Mefenpyr (-diethyl), preferably 0.1 to 10 parts by weight; and 0.05 to 50 parts by weight of Naphthalic anhydride, preferably 0.1 to 10 parts by weight, are used.

And furthermore, the above-mentioned combinations of the compounds of the. formula (I), according to the present invention, and the above-mentioned herbicides can be mixed with also the above-mentioned safeners and their application as selective herbicidal compositions can be broadened to reduce phytotoxicity and to provide wider weed—control spectrum by mixing safeners and/or other selective herbicides.

Surprisingly, some of the mixed compositions, according to the present invention show synergistic effects.

In case of using the active compounds of the formula (I) and their mixed compositions, according to the present invention, they can be directly used as such or used in formulation forms such as ready-to-use solutions, emulsions, tablets, suspensions, powders, pastes, granules or used in the use forms prepared by further dilution. The active compounds of the present invention can be applied by means of, for example, watering, spraying, atomizing, granule application etc.

The active compounds of the formula (I) and their mixed compositions, according to the present invention, can be used at any stages before and after germination of plants. They can also be taken into the soil before sowing.

The application amount of the active compounds of the formula (I) and their mixed compositions, according to the present invention, can be varied in a substantial range and are fundamentally different according to the nature of the desired effect. In case of using as herbicides, as the application amount there can be mentioned, for example, ranges of about 0.01 to about 3 kg, preferably about 0.05 to about 1 kg of the active compounds per hectare.

The preparations and applications of the compounds and their mixed compositions according to the present invention, will be described more specifically by the following examples. However, the present invention should not be restricted to them in any way.

SYNTHESIS EXAMPLE 1

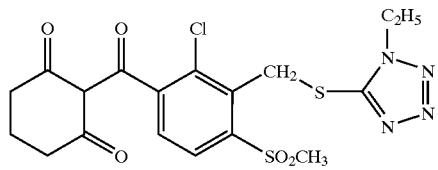

3-Oxo-1-cyclohexenyl 2-chloro-3-{[(1-ethyl-1H-tetrazol-5-yl)thio]methyl}-4-meth-ylsulfonylbenzoate (0.83 g) was dissolved in acetonitrile (20 ml), to which triethylamine (0.34 g) and acetone cyanohydrin (10 mg) were added and the mixture was stirred at room temperature for 5 hours. After distilling off the solvent, the mixture was acidified by addition of diluted hydrochloric acid and extracted with dichloromethane (150 ml). The organic layer was washed with a saturated aqueous solution of sodium chloride and dried with anhydrous magnesium sulfate. Dichloromethane was distilled off to obtain the objected 2-{2-chloro-3-{[(1-ethyl-1H-tetrazol-1-yl)thio]methyl}-4-methylsulfonylbenzoyl}cyclohexane-1,3-dione (0.75 g). mp: 67–71° C.

SYNTHESIS EXAMPLE 2

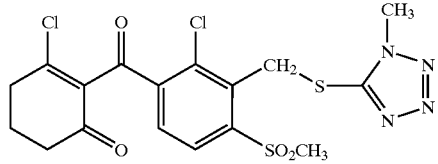

To a solution of 2-{2-chloro-4-methylsulfonyl-3-{[(1-methyl-1Htetrazol-5-yl)thio]-methyl}benzoyl}cyclohexane-1,3-dione (1.0 g) in dichloromethane (100 ml), oxalyl chloride (0.91 g) and 2 drops of N,N-dimethylformamide were added dropwise and the mixture was refluxed for 3 hours. The residue obtained by distilling off the solvent after the reaction was purified by silica gel column chromatography (eluant:ethyl acetate:hexane=7:3) to obtain the objective 3-chloro2-{2-chloro-4-methylsulfonyl-3-{[(1-methyl-1H-tetrazol-5-yl)thio]methyl}benzoyl}-2-cyclohexen-1-one (0.71 g). IR (NaCl):=1662,1310,1279, 1150 cm$^{-1}$.

SYNTHESIS EXAMPLE 3

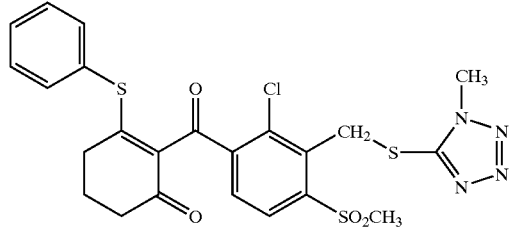

3-Chloro-2-{2-chloro-4-methylsulfonyl-3-{[(1-methyl-1H-tetrazol-5-yl)thio]meth-yl}benzoyl}-2-cyclohexen-1-one (0.75 g) and thiophenol (0.19 g) were dissolved in tetrahydrofuran (7 ml), to which a solution of triethylamine (0.19 g) in tetrahydro-furan (3 ml) was added dropwise at 5° C. and the mixture was stirred at room temperature for 4 hours. After the reaction cold water was added to the mixture, extracted with ethyl acetate (50 ml) and dried with anhydrous magnesium sulfate.

The residue obtained by distilling off the ethyl acetate was purified by silica gel column chromatography (eluant:ethyl acetate:hexane=7:3) to obtain the objective 2-{2-chloro-4-methylsulfonyl-3-{[(1-methyl-1H-tetrazol-5-yl)thio]methyl}benzoyl}-3-phenylthio-2-cyclohexen-1-one (0.61 g). mp: 76–87° C.

The compounds, obtained in the same manner as the above-mentioned Synthesis Examples 1–3, are shown in the following Tables 1–3, together with the compounds synthesized in the Synthesis Examples 1–3.

Examples of the compounds in case the compound of the formula (I) of the present invention is represented by the formula

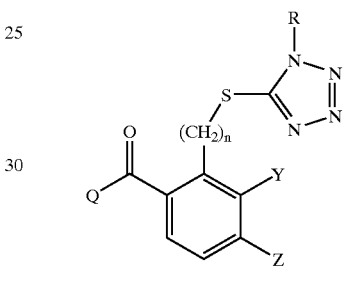

are shown in Table 1, examples of the compounds in case they are represented by the following formula

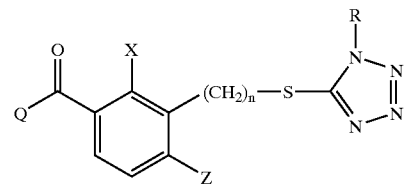

are shown in Table 2, and examples of the compounds in case they are represented by the following formula

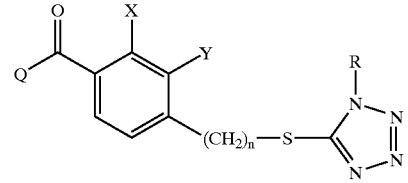

are shown in Table 3.

In Tables 1, 2 and 3,
Q1a a represents the group
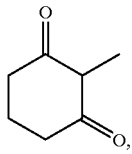
Q1b represents the group
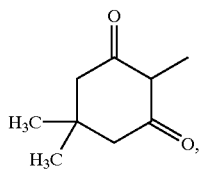
Q1c represents the group
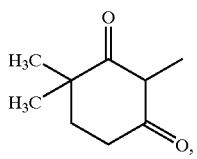
Q2 represents the group
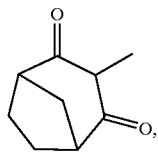
Q3a a represents the group
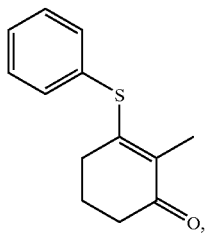
Q3b represents the group
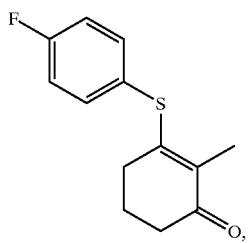
Q3c represents the group
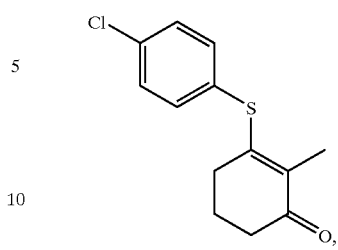
Q3d represents the group
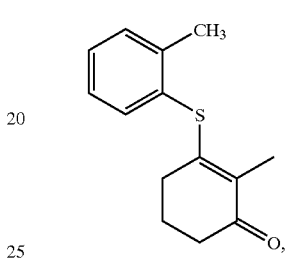
Q3e represents the group
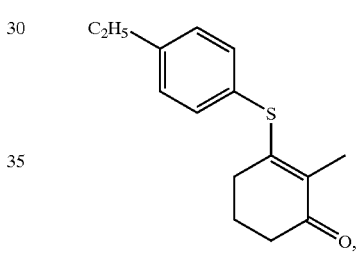
Q3f represents the group
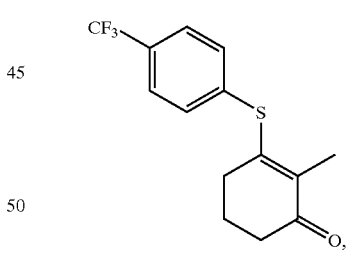
Q3g represents the group
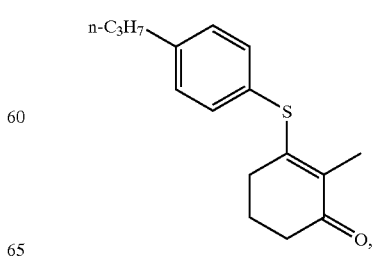

Q3h represents the group
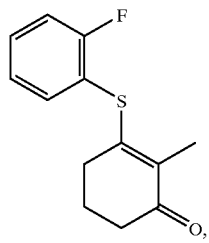
Q3i represents the group
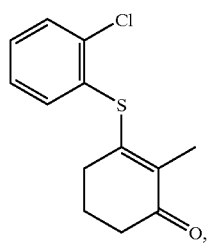
Q3j represents the group
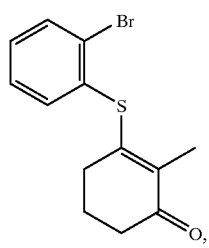
Q3k represents the group
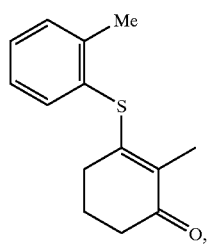
Q3l represents the group
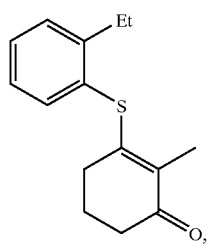
Q3m represents the group
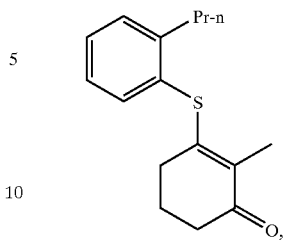
Q3n represents the group
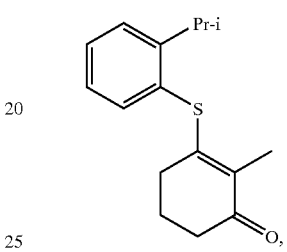
Q3o represents the group
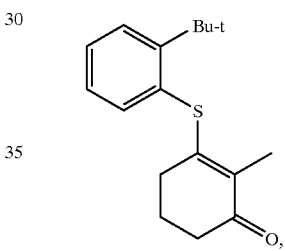
Q3p represents the group
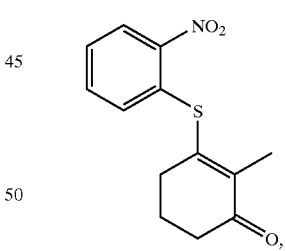
Q3q represents the group
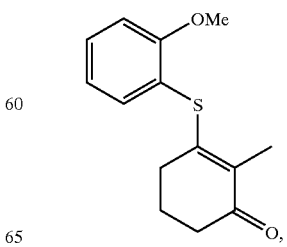

Q3r represents the group
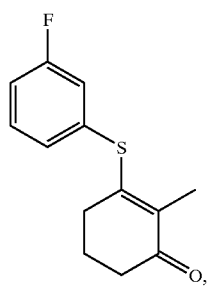
Q3s represents the group
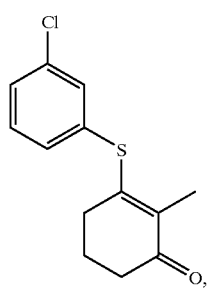
Q3t represents the group
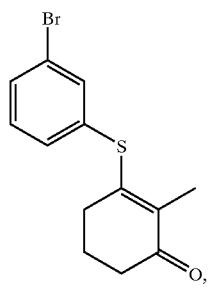
Q3u represents the group
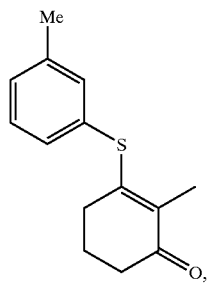
Q3v represents the group
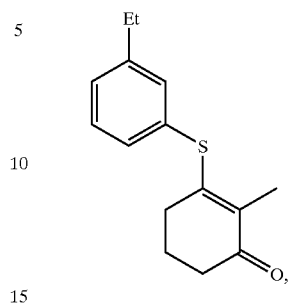
Q3w represents the group
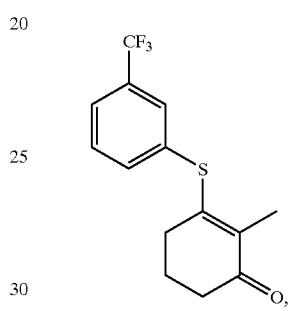
Q3x represents the group
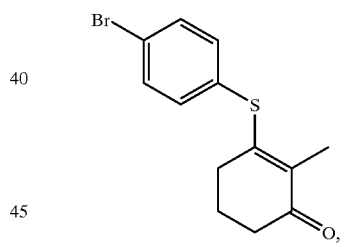
Q3y represents the group
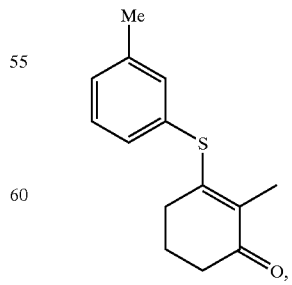

Q3z represents the group
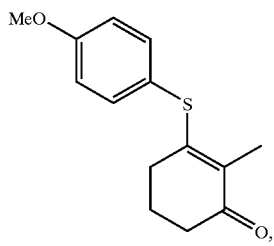
Q3za represents the group
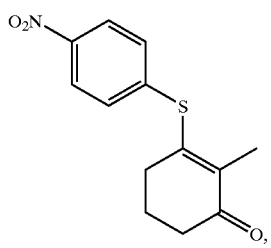
Q3zb represents the group
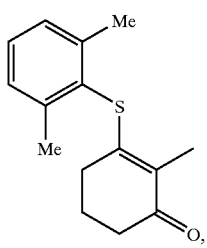
Q3zc represents the group
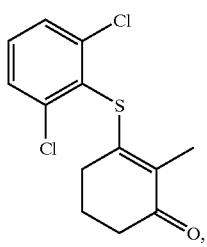
Q3zd represents the group
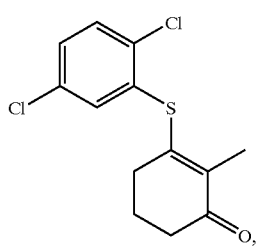
Q4a represents the group
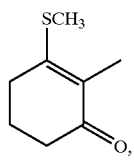
Q4b represents the group
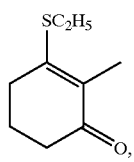
Q4c represents the group
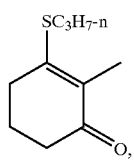
Q4d represents the group
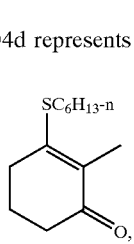
Q5a represents the group
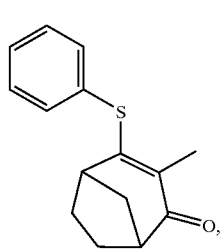
Q5b represents the group
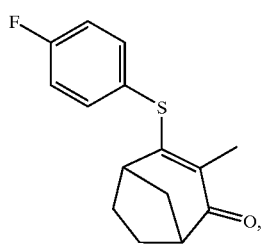

Q5c represents the group

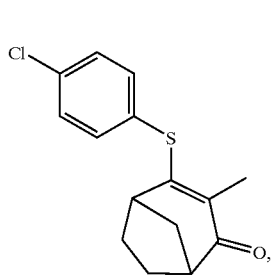

Q5d represents the group

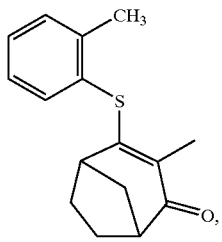

Q5e represents the group

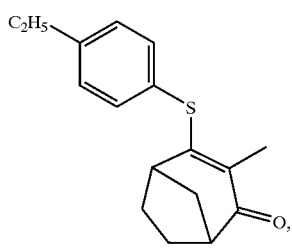

Q5f represents the group

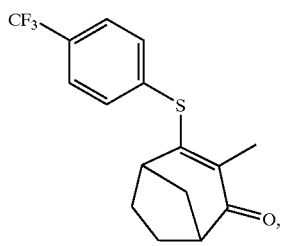

Q6a represents the group

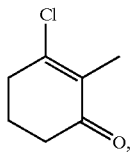

Q6b represents the group

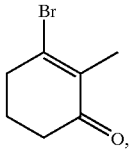

Q7 represents the group

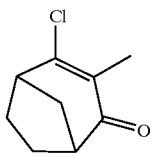

Me represents methyl, Et represents ethyl, n-Pr represents n-propyl, i-Pr represents isopropyl, n-Bu represents n-butyl, t-Bu represents tert-butyl, n-Hex represents n-hexyl, OMe represents methoxy, OEt represents ethoxy, SMe represents methylthio, SEt represents ethylthio, $SO_2Me$ represents methylsulfonyl, $SO_2Et$ represents ethylsulfonyl, $SO_2$n-Pr represents n-propylsulfonyl, $OSO_2Me$ represents methylsulfonyloxy, $OSO_2Et$ represents ethylsulfonyloxy and Ph represents phenyl.

TABLE 1

| Compound No. | Y | Z | R | n | Q | melting point (mp) or $n_D^{20}$ |
|---|---|---|---|---|---|---|
| I-1 | H | H | Me | 1 | Q1a | |
| I-2 | H | H | Me | 2 | Q1a | |
| I-3 | H | H | Me | 1 | Q2 | |
| I-4 | OMe | H | Me | 1 | Q1a | |
| I-5 | Cl | H | Me | 1 | Q1a | |
| I-6 | Me | H | Me | 1 | Q1a | |
| I-7 | H | F | Me | 1 | Q1a | |
| I-8 | H | F | Me | 1 | Q2 | |
| I-9 | H | F | Me | 1 | Q3a | |
| I-10 | H | F | Me | 1 | Q5a | |
| I-11 | H | F | Me | 1 | Q6a | |
| I-12 | H | F | Et | 1 | Q1a | |
| I-13 | H | F | cyclopropyl | | Q1a | |
| I-14 | H | Cl | Me | 1 | Q1a | |
| I-15 | H | Cl | Me | 2 | Q1a | |
| I-16 | H | Cl | Me | 1 | Q2 | |
| I-17 | H | Cl | Me | 1 | Q3a | |
| I-18 | H | Cl | Me | 1 | Q5a | |
| I-19 | H | Cl | Me | 1 | Q7 | |
| I-20 | H | Cl | Et | 1 | Q1a | |
| I-21 | H | Cl | cyclopropyl | 1 | Q1a | |

TABLE 1-continued

[Structure: benzoate with (CH2)n-S-tetrazole(R) at ortho, Y at meta, Z at para, Q as ester]

| Compound No. | Y | Z | R | n | Q | melting point (mp) or $n_D^{20}$ |
|---|---|---|---|---|---|---|
| I-22 | H | Br | Me | 1 | Q1a | 1.6212 |
| I-23 | H | Br | Me | 1 | Q2 | |
| I-24 | H | Br | Me | 1 | Q3a | |
| I-25 | H | Br | Me | 1 | Q5a | |
| I-26 | H | Br | Me | 1 | Q6a | |
| I-27 | H | Br | Et | 1 | Q1a | |
| I-28 | H | Br | cyclopropyl | 1 | Q1a | |
| I-29 | H | I | Me | 1 | Q1a | |
| I-30 | H | I | Me | 1 | Q2 | |
| I-31 | H | I | Me | 1 | Q3a | |
| I-32 | H | I | Me | 1 | Q5a | |
| I-33 | H | I | Et | 1 | Q1a | |
| I-34 | H | I | cyclopropyl | 1 | Q1a | |
| I-35 | H | Me | Me | 1 | Q1a | |
| I-36 | H | $CF_3$ | Me | 1 | Q1a | |
| I-37 | H | $CF_3$ | Me | 1 | Q2 | |
| I-38 | H | $CF_3$ | Me | 1 | Q3a | |
| I-39 | H | $CF_3$ | Me | 1 | Q5a | |
| I-40 | H | $CF_3$ | Me | 1 | Q6a | |
| I-41 | H | $CF_3$ | Me | 1 | Q7 | |
| I-42 | H | $CF_3$ | Et | 1 | Q1a | |
| I-43 | H | $CF_3$ | cyclopropyl | 1 | Q1a | |
| I-44 | H | OMe | Me | 1 | Q1a | |
| I-45 | H | OMe | Me | 1 | Q2 | |
| I-46 | H | OMe | Me | 1 | Q3a | |
| I-47 | H | OMe | Me | 1 | Q5a | |
| I-48 | H | OMe | Me | 1 | Q6a | |
| I-49 | H | OMe | Et | 1 | Q1a | |
| I-50 | H | OMe | cyclopropyl | 1 | Q1a | |
| I-51 | H | $OSO_2Me$ | Me | 1 | Q1a | |
| I-52 | H | $OSO_2Me$ | Me | 1 | Q2 | |
| I-53 | H | SMe | Me | 1 | Q1a | |
| I-54 | H | SMe | Me | 1 | Q2 | |
| I-55 | H | $SO_2Me$ | Me | 1 | Q1a | |
| I-56 | H | $SO_2Me$ | Me | 1 | Q2 | |
| I-57 | H | $SO_2Me$ | Me | 1 | Q3a | |
| I-58 | H | $SO_2Me$ | Me | 1 | Q5 | |
| I-59 | H | $SO_2Me$ | Me | 1 | Q6a | |
| I-60 | H | $SO_2Me$ | Et | 1 | Q1a | |
| I-61 | H | $SO_2Me$ | cyclopropyl | 1 | Q1a | |
| I-62 | H | $NO_2$ | Me | 1 | Q1a | |
| I-63 | H | $NO_2$ | Me | 1 | Q2 | |
| I-64 | H | $NO_2$ | Me | 1 | Q3a | |
| I-65 | H | $NO_2$ | Me | 1 | Q5a | |
| I-66 | H | $NO_2$ | Et | 1 | Q1a | |
| I-67 | H | $NO_2$ | cyclopropyl | 1 | Q1a | |
| I-68 | H | CN | Me | 1 | Q1a | |
| I-69 | H | CN | Me | 1 | Q2 | |
| I-70 | H | CN | Me | 1 | Q3a | |
| I-71 | H | CN | Me | 1 | Q5a | |
| I-72 | H | CN | Et | 1 | Q1a | |
| I-73 | H | CN | cyclopropyl | 1 | Q1a | |
| I-74 | H | $OCHF_2$ | Me | 1 | Q1a | |
| I-75 | H | $OCHF_2$ | Me | 1 | Q2 | |
| I-76 | H | $OCHF_2$ | Me | 1 | Q3a | |
| I-77 | H | $OCHF_2$ | Me | 1 | Q5a | |
| I-78 | H | $OCHF_2$ | Me | 1 | Q6a | |
| I-79 | H | $OCHF_2$ | Et | 1 | Q1a | |
| I-80 | H | $OCHF_2$ | cyclopropyl | 1 | Q1a | |
| I-81 | H | $OCF_3$ | Me | 1 | Q1a | |
| I-82 | H | $OCF_3$ | Me | 1 | Q2 | |
| I-83 | H | $OCF_3$ | Me | 1 | Q3a | |
| I-84 | H | $OCF_3$ | Me | 1 | Q5a | |
| I-85 | H | $OCF_3$ | Et | 1 | Q1a | |
| I-86 | H | $OCF_3$ | cyclopropyl | 1 | Q1a | |

TABLE 2

[Structure: benzoate with X at ortho, (CH2)n-S-tetrazole(R) at meta, Z at para, Q as ester]

| Compound No. | X | Z | R | n | Q | melting point (mp) or $n_D^{20}$ |
|---|---|---|---|---|---|---|
| II-1 | H | H | Me | 1 | Q1a | |
| II-2 | H | H | Me | 2 | Q1a | |
| II-3 | H | H | Me | 1 | Q2 | |
| II-4 | OMe | H | Me | 1 | Q1a | |
| II-5 | OMe | H | Me | 1 | Q2 | |
| II-6 | $OSO_2Me$ | H | Me | 1 | Q1a | |
| II-7 | $OSO_2Me$ | H | Me | 1 | Q2 | |
| II-8 | $NO_2$ | H | Me | 1 | Q1a | |
| II-9 | $NO_2$ | H | Me | 1 | Q2 | |
| II-10 | F | Cl | Me | 1 | Q1a | 66–72 |

TABLE 2-continued

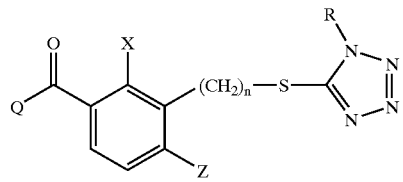

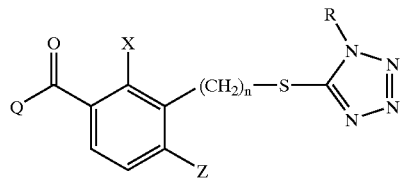

| Compound No. | X | Z | R | n | Q | melting point (mp) or $n_D^{20}$ |
|---|---|---|---|---|---|---|
| II-11 | F | Cl | Me | 1 | Q2 | |
| II-12 | F | Cl | Me | 1 | Q3a | |
| II-13 | F | Cl | Me | 1 | Q5a | |
| II-14 | F | Cl | cyclopropyl | 1 | Q1a | |
| [001b] II-15 | F | Cl | cyclopropyl | 1 | Q2 | |
| II-16 | F | Cl | cyclopropyl | 1 | Q3a | |
| II-17 | F | Cl | cyclopropyl | 1 | Q5a | |
| II-18 | Cl | Cl | Me | 1 | Q1a | 1.6010 |
| II-19 | Cl | Cl | Me | 2 | Q1a | |
| II-20 | Cl | Cl | Me | 1 | Q1b | |
| II-21 | Cl | Cl | Me | 1 | Q1c | |
| II-22 | Cl | Cl | Me | 1 | Q2 | |
| II-23 | Cl | Cl | Me | 1 | Q3a | |
| II-24 | Cl | Cl | Me | 1 | Q3b | |
| II-25 | Cl | Cl | Me | 1 | Q3d | |
| II-26 | Cl | Cl | Me | 1 | Q4a | |
| II-27 | Cl | Cl | Me | 1 | Q4b | |
| II-28 | Cl | Cl | Me | 1 | Q5a | |
| II-29 | Cl | Cl | Me | 1 | Q5c | |
| II-30 | Cl | Cl | Me | 1 | Q6a | |
| II-31 | Cl | Cl | Me | 1 | Q7 | |
| II-32 | Cl | Cl | Et | 1 | Q1a | |
| II-33 | Cl | Cl | Et | 2 | Q1a | |
| II-34 | Cl | Cl | Et | 1 | Q1b | |
| II-35 | Cl | Cl | Et | 1 | Q1c | |
| II-36 | Cl | Cl | Et | 1 | Q2 | |
| II-37 | Cl | Cl | Et | 1 | Q3a | |
| II-38 | Cl | Cl | Et | 1 | Q3f | |
| II-39 | Cl | Cl | Et | 1 | Q4a | |
| II-40 | Cl | Cl | Et | 1 | Q4b | |
| II-41 | Cl | Cl | Et | 1 | Q5a | |
| II-42 | Cl | Cl | Et | 1 | Q5d | |
| II-43 | Cl | Cl | Et | 1 | Q6a | |
| II-44 | Cl | Cl | Et | 1 | Q7 | |
| II-45 | Cl | Cl | n-Pr | 1 | Q1a | |
| II-46 | Cl | Cl | n-Pr | 1 | Q2 | |
| II-47 | Cl | Cl | n-Pr | 1 | Q3a | |
| II-48 | Cl | Cl | n-Pr | 1 | Q5a | |
| II-49 | Cl | Cl | i-Pr | 1 | Q1a | |
| II-50 | Cl | Cl | i-Pr | 1 | Q2 | |
| II-51 | Cl | Cl | i-Pr | 1 | Q3a | |
| II-52 | Cl | Cl | i-Pr | 1 | Q5a | |
| II-53 | Cl | Cl | cyclopropyl | 1 | Q1a | |
| II-54 | Cl | Cl | cyclopropyl | 1 | Q1b | |
| II-55 | Cl | Cl | cyclopropyl | 1 | Q1c | |
| II-56 | Cl | Cl | cyclopropyl | 1 | Q2 | |
| II-57 | Cl | Cl | cyclopropyl | 1 | Q3a | |
| II-58 | Cl | Cl | cyclopropyl | 1 | Q3e | |
| II-59 | Cl | Cl | cyclopropyl | 1 | Q4a | |
| II-60 | Cl | Cl | cyclopropyl | 1 | Q4b | |
| II-61 | Cl | Cl | cyclopropyl | 1 | Q5a | |
| II-62 | Cl | Cl | cyclopropyl | 1 | Q6a | |
| II-63 | Cl | Cl | cyclopropyl | 1 | Q7 | |
| II-64 | Cl | Cl | 1-ethylcyclopropyl ($C_2H_5$) | 1 | Q1a | |
| II-65 | Cl | Cl | 2,2-difluorocyclopropyl | 1 | Q1a | |
| II-66 | Cl | Cl | cyclohexyl | 1 | Q1a | |
| II-67 | Cl | Cl | cyclohexyl | 1 | Q2 | |
| II-68 | Cl | Cl | —CH=CH$_2$ | 1 | Q1a | |
| II-69 | Cl | Cl | —CH=CH$_2$ | 1 | Q1b | |
| II-70 | Cl | Cl | —CH=CH$_2$ | 1 | Q1c | |
| II-71 | Cl | Cl | —CH=CH$_2$ | 1 | Q2 | |
| II-72 | Cl | Cl | —CH=CH$_2$ | 1 | Q3a | |
| II-73 | Cl | Cl | —CH=CH$_2$ | 1 | Q4a | |
| II-74 | Cl | Cl | —CH=CH$_2$ | 1 | Q4b | |
| II-75 | Cl | Cl | —CH=CH$_2$ | 1 | Q5a | |
| II-76 | Cl | Cl | —CH=CH$_2$ | 1 | Q6a | |
| II-77 | Cl | Cl | —CH$_2$CH=CH$_2$ | 1 | Q1a | |
| II-78 | Cl | Cl | —CH$_2$CH=CH$_2$ | 1 | Q2 | |
| II-79 | Cl | Cl | —CH$_2$CH=CH$_2$ | 1 | Q3a | |
| II-80 | Cl | Cl | —CH$_2$CH=CH$_2$ | 1 | Q5a | |
| II-81 | Cl | Cl | Ph | 1 | Q1a | |
| II-82 | Cl | Cl | 2-Cl—Ph | 1 | Q1a | |
| II-83 | Cl | Cl | 2-Me—Ph | 1 | Q1a | |

TABLE 2-continued

| Compound No. | X | Z | R | n | Q | melting point (mp) or $n_D^{20}$ |
|---|---|---|---|---|---|---|
| II-84 | Cl | Cl | 3-CF$_3$—Ph | 1 | Q1a | |
| II-85 | Cl | Cl | CH$_2$CH$_2$F | 1 | Q1a | |
| II-86 | Cl | Cl | CH$_2$CH$_2$F | 1 | | |
| II-87 | Cl | Cl | CH$_2$CH$_2$F | 1 | Q3a | |
| II-88 | Cl | Cl | CH$_2$CH$_2$F | 1 | Q5a | |
| II-89 | Cl | Cl | CH$_2$CH$_2$F | 1 | Q6a | |
| II-90 | Cl | Cl | CH$_2$CH$_2$Cl | 1 | Q1a | |
| II-91 | Cl | Cl | CH$_2$CH$_2$Cl | 1 | Q2 | |
| II-92 | Cl | Cl | CH$_2$CH$_2$Cl | 1 | Q3a | |
| II-93 | Cl | Cl | CH$_2$CH$_2$Cl | 1 | Q5a | |
| II-94 | Cl | Cl | CH$_2$CF$_3$ | 1 | Q1a | |
| II-95 | Cl | Cl | CH$_2$CF$_3$ | 1 | Q1b | |
| II-96 | Cl | Cl | CH$_2$CF$_3$ | 1 | Q1c | |
| II-97 | Cl | Cl | CH$_2$CF$_3$ | 1 | Q2 | |
| II-98 | Cl | Cl | CH$_2$CF$_3$ | 1 | Q3a | |
| II-99 | Cl | Cl | CH$_2$CF$_3$ | 1 | Q4a | |
| II-100 | Cl | Cl | CH$_2$CF$_3$ | 1 | Q4b | |
| II-101 | Cl | Cl | CH$_2$CF$_3$ | 1 | Q5a | |
| II-102 | Cl | Cl | CH$_2$CF$_3$ | 1 | Q6a | |
| II-103 | Cl | Cl | CH$_2$CF$_3$ | 1 | Q7 | |
| II-104 | Cl | Cl | CH$_2$CF$_2$CF$_3$ | 1 | Q1a | |
| II-105 | Cl | Cl | CH$_2$CF$_2$CF$_3$ | 1 | Q2 | |
| II-106 | Cl | Cl | CH$_2$CF$_2$CF$_3$ | 1 | Q3a | |
| II-107 | Cl | Cl | CH$_2$CF$_2$CF$_3$ | 1 | Q5a | |
| II-108 | Cl | Cl | CH$_2$CH$_2$CH$_2$F | 1 | Q1a | |
| II-109 | Cl | Cl | CH$_2$CH$_2$CH$_2$F | 1 | Q2 | |
| II-110 | Cl | Cl | CH$_2$CH$_2$CH$_2$F | 1 | Q3a | |
| II-111 | Cl | Cl | CH$_2$CH$_2$CH$_2$F | 1 | Q5a | |
| II-112 | Cl | SMe | Me | 1 | Q1a | |
| II-113 | Cl | SMe | Me | 1 | Q2 | |
| II-114 | Cl | SMe | Et | 1 | Q1a | |
| II-115 | Cl | SMe | cyclopropyl | 1 | Q1a | |
| II-116 | Cl | SMe | —CH=CH$_2$ | 1 | Q1a | |
| II-117 | Cl | SO$_2$Me | Me | 1 | Q1a | 78–84 |
| II-118 | Cl | SO$_2$Me | Me | 1 | Q1a | |
| II-119 | Cl | SO$_2$Me | Me | 1 | Q1b | |
| II-120 | Cl | SO$_2$Me | Me | 1 | Q1c | |
| II-121 | Cl | SO$_2$Me | Me | 1 | Q2 | 60–63 |
| II-122 | Cl | SO$_2$Me | Me | 1 | Q3a | 76–87 |
| II-123 | Cl | SO$_2$Me | Me | 1 | Q3c | 210–211 |
| II-124 | Cl | SO$_2$Me | Me | 1 | Q3 | |
| II-125 | Cl | SO$_2$Me | Me | 1 | Q4a | 79–82 |
| II-126 | Cl | SO$_2$Me | Me | 1 | Q4b | |
| II-127 | Cl | SO$_2$Me | Me | 1 | Q5a | |
| II-128 | Cl | SO$_2$Me | Me | 1 | Q5f | |
| II-129 | Cl | SO$_2$Me | Me | 1 | Q6a | |
| II-130 | Cl | SO$_2$Me | Me | 1 | Q7 | |
| II-131 | Cl | SO$_2$Me | Et | 1 | Q1a | 67–71 |
| II-132 | Cl | SO$_2$Me | Et | 2 | Q1a | |
| II-133 | Cl | SO$_2$Me | Et | 1 | Q1b | |
| II-134 | Cl | SO$_2$Me | Et | 1 | Q1c | |
| II-135 | Cl | SO$_2$Me | Et | 1 | Q2 | |
| II-136 | Cl | SO$_2$Me | Et | 1 | Q3a | |
| II-137 | Cl | SO$_2$Me | Et | 1 | Q3b | |
| II-138 | Cl | SO$_2$Me | Et | 1 | Q4a | |
| II-139 | Cl | SO$_2$Me | Et | 1 | Q4b | |
| II-140 | Cl | SO$_2$Me | Et | 1 | Q5a | |
| II-141 | Cl | SO$_2$Me | Et | 1 | Q5b | |
| II-142 | Cl | SO$_2$Me | Et | 1 | Q6a | |
| II-143 | Cl | SO$_2$Me | Et | 1 | Q7 | |
| II-144 | Cl | SO$_2$Me | n-Pr | 1 | Q1a | 142–145 |
| II-145 | Cl | SO$_2$Me | n-Pr | 1 | Q2 | |
| II-146 | Cl | SO$_2$Me | n-Pr | 1 | Q3a | |
| II-147 | Cl | SO$_2$Me | n-Pr | 1 | Q5a | |
| II-148 | Cl | SO$_2$Me | i-Pr | 1 | Q1a | 69–73 |
| II-149 | Cl | SO$_2$Me | i-Pr | 1 | Q2 | |
| II-150 | Cl | SO$_2$Me | i-Pr | 1 | Q3a | |
| II-151 | Cl | SO$_2$Me | i-Pr | 1 | Q5a | |
| II-152 | Cl | SO$_2$Me | cyclopropyl | 1 | Q1a | 79–84 |
| II-153 | Cl | SO$_2$Me | cyclopropyl | 1 | Q1b | |
| II-154 | Cl | SO$_2$Me | cyclopropyl | 1 | Q1c | |
| II-155 | Cl | SO$_2$Me | cyclopropyl | 1 | Q2 | |
| II-156 | Cl | SO$_2$Me | cyclopropyl | 1 | Q3a | |
| II-157 | Cl | SO$_2$Me | cyclopropyl | 1 | Q3d | |
| II-158 | Cl | SO$_2$Me | cyclopropyl | 1 | Q4a | |
| II-159 | Cl | SO$_2$Me | cyclopropyl | 1 | Q4b | |
| II-160 | Cl | SO$_2$Me | cyclopropyl | 1 | Q5a | |
| II-161 | Cl | SO$_2$Me | cyclopropyl | 1 | Q6a | |
| II-162 | Cl | SO$_2$Me | cyclopropyl | 1 | Q7 | |
| II-163 | Cl | SO$_2$Me | 1-methylcyclopropyl | 1 | Q1a | |
| II-164 | Cl | SO$_2$Me | 2-methylcyclopropyl | 1 | Q2 | |
| II-165 | Cl | SO$_2$Me | 2-n-propylcyclopropyl | 1 | Q1a | |

TABLE 2-continued

Structure: benzene ring with COQ, X substituent, (CH₂)ₙ-S-tetrazole (with R on N), and Z substituent.

| Compound No. | X | Z | R | n | Q | melting point (mp) or $n_D^{20}$ |
|---|---|---|---|---|---|---|
| II-166 | Cl | SO₂Me | cyclohexyl-H | 1 | Q1a | |
| II-167 | Cl | SO₂Me | cyclohexyl-H | 1 | Q2 | |
| II-168 | Cl | SO₂Me | —CH=CH₂ | 1 | Q1a | |
| II-169 | Cl | SO₂Me | —CH=CH₂ | 1 | Q1b | |
| II-170 | Cl | SO₂Me | —CH=CH₂ | 1 | Q1c | |
| II-171 | Cl | SO₂Me | —CH=CH₂ | 1 | Q2 | |
| II-172 | Cl | SO₂Me | —CH=CH₂ | 1 | Q3a | |
| II-173 | Cl | SO₂Me | —CH=CH₂ | 1 | Q4a | |
| II-174 | Cl | SO₂Me | —CH=CH₂ | 1 | Q4b | |
| II-175 | Cl | SO₂Me | —CH=CH₂ | 1 | Q5a | |
| II-176 | Cl | SO₂Me | —CH=CH₂ | 1 | Q6a | |
| II-177 | Cl | SO₂Me | —CH₂CH=CH₂ | 1 | Q1a | 63–68 |
| II-178 | Cl | SO₂Me | —CH₂CH=CH₂ | 1 | Q2 | |
| II-179 | Cl | SO₂Me | —CH₂CH=CH₂ | 1 | Q3a | |
| II-180 | Cl | SO₂Me | —CH₂CH=CH₂ | 1 | Q5a | |
| II-181 | Cl | SO₂Me | Ph | 1 | Q1a | |
| II-182 | Cl | SO₂Me | 4-F—Ph | 1 | Q1a | |
| II-183 | Cl | SO₂Me | 2-Cl—Ph | 1 | Q1a | 84–90 |
| II-184 | Cl | SO₂Me | 3-Et—Ph | 1 | Q | |
| II-185 | Cl | SO₂Me | 4-NO₂—Ph | 1 | Q1a | |
| II-186 | Cl | SO₂Me | CH₂CH₂F | 1 | Q1a | |
| II-187 | Cl | SO₂Me | CH₂CH₂F | 1 | Q2 | |
| II-188 | Cl | SO₂Me | CH₂CH₂F | 1 | Q3a | |
| II-189 | Cl | SO₂Me | CH₂CH₂F | 1 | Q5a | |
| II-190 | Cl | SO₂Me | CH₂CH₂Cl | 1 | Q1a | |
| II-191 | Cl | SO₂Me | CH₂CH₂Cl | 1 | Q2 | |
| II-192 | Cl | SO₂Me | CH₂CH₂Cl | 1 | Q3a | |
| II-193 | Cl | SO₂Me | CH₂CH₂Cl | 1 | Q5a | |
| II-194 | Cl | SO₂Me | CH₂CF₃ | 1 | Q1a | 82–87 |
| II-195 | Cl | SO₂Me | CH₂CF₃ | 1 | Q1b | |
| II-196 | Cl | SO₂Me | CH₂CF₃ | 1 | Q1c | |
| II-197 | Cl | SO₂Me | CH₂CF₃ | 1 | Q2 | |
| II-198 | Cl | SO₂Me | CH₂CF₃ | 1 | Q3a | |
| II-199 | Cl | SO₂Me | CH₂CF₃ | 1 | Q4a | |
| II-200 | Cl | SO₂Me | CH₂CF₃ | 1 | Q4b | |
| II-201 | Cl | SO₂Me | CH₂CF₃ | 1 | Q5a | |
| II-202 | Cl | SO₂Me | CH₂CF₃ | 1 | Q6a | |
| II-203 | Cl | SO₂Me | CH₂CF₃ | 1 | Q7 | |
| II-204 | Cl | SO₂Me | CH₂CF₂CF₃ | 1 | Q1a | |
| II-205 | Cl | SO₂Me | CH₂CF₂CF₃ | 1 | Q2 | |
| II-206 | Cl | SO₂Me | CH₂CF₂CF₃ | 1 | Q3a | |
| II-207 | Cl | SO₂Me | CH₂CH₂CH₂F | 1 | Q5a | |
| II-208 | Cl | SO₂Me | CH₂CH₂CH₂F | 1 | Q1a | |
| II-209 | Cl | SO₂Me | CH₂CH₂CH₂F | 1 | Q2 | |
| II-210 | Cl | SO₂Me | CH₂CH₂CH₂F | 1 | Q3a | |
| II-211 | Cl | SO₂Me | CH₂CH₂CH₂F | 1 | Q5a | |
| II-212 | Cl | SO₂Et | Me | 1 | Q1a | 70–74 |
| II-213 | Cl | SO₂Et | Me | 1 | Q2 | |
| II-214 | Cl | SO₂Et | Me | 1 | Q3a | |
| II-215 | Cl | SO₂Et | Me | 1 | Q5a | |
| II-216 | Cl | SO₂Et | Me | 1 | Q6a | |
| II-217 | Cl | SO₂Et | Me | 1 | Q7 | |
| II-218 | Cl | SO₂Et | Et | 1 | Q1a | |
| II-219 | Cl | SO₂Et | Et | 1 | Q2 | |
| II-220 | Cl | SO₂Et | cyclopropyl | 1 | Q1a | |
| II-221 | Cl | SO₂Et | cyclopropyl | 1 | Q2 | |
| II-222 | Cl | SO₂Et | 1-methylcyclopropyl (CH₃) | 1 | Q1a | |
| II-223 | Cl | SO₂Et | —CH=CH₂ | 1 | Q1a | |
| II-224 | Cl | SO₂Et | —CH=CH₂ | 1 | Q2 | |
| II-225 | Cl | SO₂n-Pr | cyclopropyl | 1 | Q1a | |
| II-226 | Br | Br | Me | 1 | Q1a | 72–179 |
| II-227 | Br | Br | Me | 1 | Q1b | |
| II-228 | Br | Br | Me | 1 | Q1c | |
| II-229 | Br | Br | Me | 1 | Q2 | |
| II-230 | Br | Br | Me | 1 | Q3a | |
| II-231 | Br | Br | Me | 1 | Q3c | |
| II-232 | Br | Br | Me | 1 | Q3f | |
| II-233 | Br | Br | Me | 1 | Q4a | |
| II-234 | Br | Br | Me | 1 | Q4b | |
| II-235 | Br | Br | Me | 1 | Q5a | |
| II-236 | Br | Br | Me | 1 | Q5e | |
| II-237 | Br | Br | Me | 1 | Q6a | |
| II-238 | Br | Br | Me | 1 | Q7 | |
| II-239 | Br | Br | Et | 1 | Q1a | |
| II-240 | Br | Br | Et | 1 | Q2 | |
| II-241 | Br | Br | Et | 1 | Q3a | |
| II-242 | Br | Br | Et | 1 | Q3d | |
| II-243 | Br | Br | Et | 1 | Q5a | |
| II-244 | Br | Br | n-Pr | 1 | Q1a | |
| II-245 | Br | Br | n-Pr | 1 | Q2 | |
| II-246 | Br | Br | i-Pr | 1 | Q1a | |
| II-247 | Br | Br | i-Pr | 1 | Q2 | |
| II-248 | Br | Br | cyclopropyl | 1 | Q1a | |
| II-249 | Br | Br | cyclopropyl | 1 | Q1b | |
| II-250 | Br | Br | cyclopropyl | 1 | Q1c | |
| II-251 | Br | Br | cyclopropyl | 1 | Q2 | |
| II-252 | Br | Br | cyclopropyl | 1 | Q3a | |
| II-253 | Br | Br | cyclopropyl | 1 | Q4a | |

TABLE 2-continued

| Compound No. | X | Z | R | n | Q | melting point (mp) or $n_D^{20}$ |
|---|---|---|---|---|---|---|
| II-254 | Br | Br |  | 1 | Q4b | |
| II-255 | Br | Br | 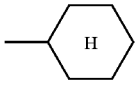 | 1 | Q5a | |
| II-256 | Br | Br |  | 1 | Q1a | |
| II-257 | Br | Br | —CH=CH$_2$ | 1 | Q1a | |
| II-258 | Br | Br | —CH=CH$_2$ | 1 | Q2 | |
| II-259 | Br | Br | —CH=CH$_2$ | 1 | Q3a | |
| II-260 | Br | Br | —CH=CH$_2$ | 1 | Q5a | |
| II-261 | Br | Br | —CH$_2$CH=CH$_2$ | 1 | Q1a | |
| II-262 | Br | Br | —CH$_2$CH=CH$_2$ | 1 | Q2 | |
| II-263 | Br | Br | Ph | 1 | Q1a | |
| II-264 | Br | Br | 2-Cl—Ph | 1 | Q1a | |
| II-265 | Br | Br | 2-CF$_3$—Ph | 1 | Q1a | |
| II-266 | Br | Br | CH$_2$CH$_2$F | 1 | Q1a | |
| II-267 | Br | Br | CH$_2$CH$_2$F | 1 | Q2 | |
| II-268 | Br | Br | CH$_2$CH$_2$Cl | 1 | Q1a | |
| II-269 | Br | Br | CH$_2$CH$_2$Cl | 1 | Q2 | |
| II-270 | Br | Br | CH$_2$CF$_3$ | 1 | Q1a | |
| II-271 | Br | Br | CH$_2$CF$_3$ | 1 | Q2 | |
| II-272 | Br | Br | CH$_2$CF$_3$ | 1 | Q3a | |
| II-273 | Br | Br | CH$_2$CF$_3$ | 1 | Q5a | |
| II-274 | Br | Br | CH$_2$CF$_2$CF$_3$ | 1 | Q1a | |
| II-275 | Br | Br | CH$_2$CH$_2$CH$_2$F | 1 | Q1a | |
| II-276 | Br | SO$_2$Me | Me | 1 | Q1a | 87–90 |
| II-277 | Br | SO$_2$Me | Me | 1 | Q2 | |
| II-278 | Br | SO$_2$Me | Et | 1 | Q1a | |
| II-279 | Br | SO$_2$Me |  | 1 | Q1a | |
| II-280 | Br | SO$_2$Me |  | 1 | Q1a | |
| II-281 | Br | SO$_2$Me | —CH=CH$_2$ | 1 | Q1a | |
| II-282 | OMe | Cl | Me | 1 | Q1a | 1.6131 |
| II-283 | OMe | Cl | Me | 1 | Q1b | |
| II-284 | OMe | Cl | Me | 1 | Q1c | |
| II-285 | OMe | Cl | Me | 1 | Q2 | |
| II-286 | OMe | Cl | Me | 1 | Q3a | |
| II-287 | OMe | Cl | Me | 1 | Q4a | |
| II-288 | OMe | Cl | Me | 1 | Q4b | |
| II-289 | OMe | Cl | Me | 1 | Q5a | |
| II-290 | OMe | Cl | Me | 1 | Q6a | |
| II-291 | OMe | Cl | Et | 1 | Q1a | |
| II-292 | OMe | Cl | Et | 1 | Q2 | |
| II-293 | OMe | Cl | Et | 1 | Q3a | |
| II-294 | OMe | Cl | Et | 1 | Q5a | |
| II-295 | OMe | Cl | Et | 1 | Q7 | |
| II-296 | OMe | Cl | n-Pr | 1 | Q1a | |
| II-297 | OMe | Cl | n-Pr | 1 | Q2 | |
| II-298 | OMe | Cl | i-Pr | 1 | Q1a | |
| II-299 | OMe | Cl | i-Pr | 1 | Q2 | |
| II-300 | OMe | Cl |  | 1 | Q1a | |
| II-301 | OMe | Cl |  | 1 | Q1b | |
| II-302 | OMe | Cl |  | 1 | Q1c | |
| II-303 | OMe | Cl |  | 1 | Q2 | |
| II-304 | OMe | Cl |  | 1 | Q3a | |
| II-305 | OMe | Cl |  | 1 | Q4a | |
| II-306 | OMe | Cl |  | 1 | Q4b | |
| II-307 | OMe | Cl |  | 1 | Q5a | |
| II-308 | OMe | Cl |  | 1 | Q1a | |
| II-309 | OMe | Cl |  | 1 | Q1a | |
| II-310 | OMe | Cl | —CH=CH$_2$ | 1 | Q1a | |
| II-311 | OMe | Cl | —CH=CH$_2$ | 1 | Q2 | |
| II-312 | OMe | Cl | —CH=CH$_2$ | 1 | Q3a | |
| II-313 | OMe | Cl | —CH=CH$_2$ | 1 | Q5a | |
| II-314 | OMe | Cl | —CH$_2$CH=CH$_2$ | 1 | Q1a | |
| II-315 | OMe | Cl | —CH$_2$CH=CH$_2$ | 1 | Q2 | |
| II-316 | OMe | Cl | Ph | 1 | Q1a | |
| II-317 | OMe | Cl | 2-Cl—Ph | 1 | Q1a | |
| II-318 | OMe | Cl | CH$_2$CH$_2$F | 1 | Q1a | |
| II-319 | OMe | Cl | CH$_2$CH$_2$F | 1 | Q2 | |
| II-320 | OMe | Cl | CH$_2$CH$_2$Cl | 1 | Q1a | |
| II-321 | OMe | Cl | CH$_2$CH$_2$Cl | 1 | Q2 | |
| II-322 | OMe | Cl | CH$_2$CF$_3$ | 1 | Q1a | |
| II-323 | OMe | Cl | CH$_2$CF$_3$ | 1 | Q2 | |
| II-324 | OMe | Cl | CH$_2$CF$_3$ | 1 | Q3a | |
| II-325 | OMe | Cl | CH$_2$CF$_3$ | 1 | Q5a | |
| II-326 | OMe | Cl | CH$_2$CF$_2$CF$_3$ | 1 | Q1a | |
| II-327 | OMe | Cl | CH$_2$CH$_2$CH$_2$F | 1 | Q1a | |
| II-328 | OCHF$_2$ | Cl | Me | 1 | Q1a | |
| II-329 | OCHF$_2$ | Cl | Me | 1 | Q2 | |
| II-330 | OCHF$_2$ | Cl | Me | 1 | Q3a | |
| II-331 | OCHF$_2$ | Cl | Et | 1 | Q1a | |
| II-332 | OCHF$_2$ | Cl |  | 1 | Q1a | |

TABLE 2-continued

| Compound No. | X | Z | R | n | Q | melting point (mp) or $n_D^{20}$ |
|---|---|---|---|---|---|---|
| II-333 | OCHF$_2$ | Cl | —CH=CH$_2$ | 1 | Q1a | |
| II-334 | OCH$_2$CF$_3$ | Cl | Me | 1 | Q1a | |
| II-335 | OCH$_2$CF$_3$ | Cl | Me | 1 | Q2 | |
| II-336 | OCH$_2$CF$_3$ | Cl | Et | 1 | Q1a | |
| II-337 | SMe | Cl | Me | 1 | Q1a | |
| II-338 | SMe | Cl | Me | 1 | Q2 | |
| II-339 | SMe | Cl | Et | 1 | Q1a | |
| II-340 | SMe | Cl |  | 1 | Q1a | |
| II-341 | SMe | Cl | —CH=CH$_2$ | 1 | Q1a | |
| II-342 | SMe | SMe | Me | 1 | Q1a | |
| II-343 | SMe | SMe | Me | 1 | Q2 | |
| II-344 | SMe | SMe | Et | 1 | Q1a | |
| II-345 | SMe | SMe |  | 1 | Q1a | |
| II-346 | SMe | SMe | —CH=CH$_2$ | 1 | Q1a | |
| II-347 | SO$_2$Me | Cl | Me | 1 | Q1a | |
| II-348 | SO$_2$Me | Cl | Me | 1 | Q2 | |
| II-349 | SO$_2$Me | Cl | Et | 1 | Q1a | |
| II-350 | SO$_2$Me | Cl |  | 1 | Q1a | |
| II-351 | SO$_2$Me | Cl | —CH=CH$_2$ | 1 | Q1a | |
| II-352 | SO$_2$Me | SO$_2$Me | Me | 1 | Q1a | |
| II-353 | SO$_2$Me | SO$_2$Me | Me | 1 | Q2 | |
| II-354 | SO$_2$Me | SO$_2$Me | Et | 1 | Q1a | |
| II-355 | SO$_2$Me | SO$_2$Me |  | 1 | Q1a | |
| II-356 | SO$_2$Me | SO$_2$Me | —CH=CH$_2$ | 1 | Q1a | |
| II-357 | Me | SO$_2$Me | Me | 1 | Q1a | 69–71 |
| II-358 | Me | SO$_2$Me | Me | 2 | Q1a | |
| II-359 | Me | SO$_2$Me | Me | 1 | Q1b | |
| II-360 | Me | SO$_2$Me | Me | 1 | Q1c | |
| II-361 | Me | SO$_2$Me | Me | 1 | Q2 | |
| II-362 | Me | SO$_2$Me | Me | 1 | Q3a | |
| II-363 | Me | SO$_2$Me | Me | 1 | Q3c | |
| II-364 | Me | SO$_2$Me | Me | 1 | Q3d | |
| II-365 | Me | SO$_2$Me | Me | 1 | Q4a | |
| II-366 | Me | SO$_2$Me | Me | 1 | Q4b | |
| II-367 | Me | SO$_2$Me | Me | 1 | Q5a | |
| II-368 | Me | SO$_2$Me | Me | 1 | Q5c | |
| II-369 | Me | SO$_2$Me | Me | 1 | Q6a | |
| II-370 | Me | SO$_2$Me | Me | 1 | Q7 | |
| II-371 | Me | SO$_2$Me | Et | 1 | Q1a | |
| II-372 | Me | SO$_2$Me | Et | 1 | Q2 | |
| II-373 | Me | SO$_2$Me | Et | 1 | Q3a | |
| II-374 | Me | SO$_2$Me | Et | 1 | Q3b | |
| II-375 | Me | SO$_2$Me | Et | 1 | Q5a | |
| II-376 | Me | SO$_2$Me | n-Pr | 1 | Q1a | |
| II-377 | Me | SO$_2$Me | n-Pr | 1 | Q2 | |
| II-378 | Me | SO$_2$Me | i-Pr | 1 | Q1a | |
| II-379 | Me | SO$_2$Me | i-Pr | 1 | Q2 | |
| II-380 | Me | SO$_2$Me |  | 1 | Q1a | |
| II-381 | Me | SO$_2$Me |  | 1 | Q1b | |
| II-382 | Me | SO$_2$Me |  | 1 | Q1c | |
| II-383 | Me | SO$_2$Me |  | 1 | Q2 | |
| II-384 | Me | SO$_2$Me |  | 1 | Q3a | |
| II-385 | Me | SO$_2$Me |  | 1 | Q4a | |
| II-386 | Me | SO$_2$Me |  | 1 | Q4b | |
| II-387 | Me | SO$_2$Me |  | 1 | Q5a | |
| II-388 | Me | SO$_2$Me |  | 1 | Q1a | |
| II-389 | Me | SO$_2$Me |  | 1 | Q1a | |
| II-390 | Me | SO$_2$Me | H (cyclohexyl) | 1 | Q1a | |
| II-391 | Me | SO$_2$Me | —CH=CH$_2$ | 1 | Q1a | |
| II-392 | Me | SO$_2$Me | —CH=CH$_2$ | 1 | Q2 | |
| II-393 | Me | SO$_2$Me | —CH=CH$_2$ | 1 | Q3a | |
| II-394 | Me | SO$_2$Me | —CH=CH$_2$ | 1 | Q5a | |
| II-395 | Me | SO$_2$Me | —CH$_2$CH=CH$_2$ | 1 | Q1a | |
| II-396 | Me | SO$_2$Me | —CH$_2$CH=CH$_2$ | 1 | Q2 | |
| II-397 | Me | SO$_2$Me | Ph | 1 | Q1a | |
| II-398 | Me | SO$_2$Me | 2-Cl—Ph | 1 | Q1a | |
| II-399 | Me | SO$_2$Me | 4-NO$_2$—Ph | 1 | Q1a | |
| II-400 | Me | SO$_2$Me | CH$_2$CH$_2$F | 1 | Q1a | |
| II-401 | Me | SO$_2$Me | CH$_2$CH$_2$F | 1 | Q2 | |
| II-402 | Me | SO$_2$Me | CH$_2$CH$_2$Cl | 1 | Q1a | |
| II-403 | Me | SO$_2$Me | CH$_2$CH$_2$Cl | 1 | Q2 | |
| II-404 | Me | SO$_2$Me | CH$_2$CF$_3$ | 1 | Q1a | |
| II-405 | Me | SO$_2$Me | CH$_2$CF$_3$ | 1 | Q2 | |
| II-406 | Me | SO$_2$Me | CH$_2$CF$_3$ | 1 | Q3a | |
| II-407 | Me | SO$_2$Me | CH$_2$CF$_3$ | 1 | Q5a | |
| II-408 | Me | SO$_2$Me | CH$_2$CF$_2$CF$_3$ | 1 | Q1a | |
| II-409 | Me | SO$_2$Me | CH$_2$CH$_2$CH$_2$F | 1 | Q1a | |
| II-410 | CN | SO$_2$Me | Me | 1 | Q1a | 54–60 |
| II-411 | CN | SO$_2$Me | Me | 1 | Q2 | |
| II-412 | CN | SO$_2$Me | Me | 1 | Q3a | |
| II-413 | CN | SO$_2$Me | Et | 1 | Q1a | |

TABLE 2-continued

| Compound No. | X | Z | R | n | Q | melting point (mp) or $n_D^{20}$ |
|---|---|---|---|---|---|---|
| II-414 | CN | SO₂Me |  | 1 | Q1a | |
| II-415 | CN | SO₂Me |  | 1 | Q5a | |
| II-416 | Cl | SEt | Me | 1 | Q1a | |
| II-417 | Cl | SO₂Me | Me | 1 | Q3g | |
| II-418 | Cl | SO₂Me | Me | 1 | Q4c | |
| II-419 | Cl | SO₂Me | Me | 1 | Q4d | |
| II-420 | Cl | SO₂Me | Me | 1 | Q6b | |
| II-421 | Cl | SO₂Me | n-Bu | 1 | Q1a | |
| II-422 | Cl | SO₂Me | n-Hex | 1 | Q1a | |
| II-423 | Cl | SO₂Me | —CH₂CH=CHCH₃ | 1 | Q1a | |
| II-424 | Cl | SO₂Me | —(CH₂)₄CH=CH₂ | 1 | Q1a | |
| II-425 | Cl | SO₂Me | 4-(n-Pr)—Ph | 1 | Q1a | |
| II-426 | Cl | SO₂Me | 4-(CH₂CH₂Cl)—Ph | 1 | Q1a | |
| II-427 | Cl | SO₂Me | —(CH₂)₄Cl | 1 | Q1a | |
| II-428 | OEt | Cl | Me | 1 | Q1a | |
| II-429 | OSO₂Me | Cl | Me | 1 | Q1a | |
| II-430 | OSO₂Et | Cl | Me | 1 | Q1a | |
| II-431 | Et | SO₂Me | Me | 1 | Q1a | |
| II-432 | Cl | SO₂Me | Me | 1 | Q3h | |
| II-433 | Cl | SO₂Me | Me | 1 | Q3i | 128–131 |
| II-434 | Cl | SO₂Me | Me | 1 | Q3j | |
| II-435 | Cl | SO₂Me | Me | 1 | Q3d | 85–91 |
| II-436 | Cl | SO₂Me | Me | 1 | Q3k | |
| II-437 | Cl | SO₂Me | Me | 1 | Q3l | |
| II-438 | Cl | SO₂Me | Me | 1 | Q3m | |
| II-439 | Cl | SO₂Me | Me | 1 | Q3n | |
| II-440 | Cl | SO₂Me | Me | 1 | Q3o | |
| II-441 | Cl | SO₂Me | Me | 1 | Q3p | |
| II-442 | Cl | SO₂Me | Me | 1 | Q3q | |
| II-443 | Cl | SO₂Me | Me | 1 | Q3r | |
| II-444 | Cl | SO₂Me | Me | 1 | Q3s | |
| II-445 | Cl | SO₂Me | Me | 1 | Q3t | |
| II-446 | Cl | SO₂Me | Me | 1 | Q3u | |
| II-447 | Cl | SO₂Me | Me | 1 | Q3v | |
| II-448 | Cl | SO₂Me | Me | 1 | Q3w | |
| II-449 | Cl | SO₂Me | Me | 1 | Q3b | |
| II-450 | Cl | SO₂Me | Me | 1 | Q3x | |
| II-451 | Cl | SO₂Me | Me | 1 | Q3y | 208–209 |
| II-452 | Cl | SO₂Me | Me | 1 | Q3f | |
| II-453 | Cl | SO₂Me | Me | 1 | Q3z | |
| II-454 | Cl | SO₂Me | Me | 1 | Q3za | |
| II-455 | Cl | SO₂Me | Me | 1 | Q3zb | |
| II-456 | Cl | SO₂Me | Me | 1 | Q3zc | |
| II-457 | Cl | SO₂Me | Me | 1 | Q3zd | |

TABLE 3

| Compound No. | X | Y | R | n | Q | melting point (mp) or $n_D^{20}$ |
|---|---|---|---|---|---|---|
| III-1 | H | H | Me | 1 | Q1a | |
| III-2 | H | H | Me | 2 | Q1a | |
| III-3 | H | H | Me | 1 | Q2 | |
| III-4 | H | OMe | Me | 1 | Q1a | |
| III-5 | H | NO₂ | Me | 1 | Q1a | |
| III-6 | F | H | Me | 1 | Q1a | |
| III-7 | F | H | Me | 1 | Q2 | |
| III-8 | F | H | Et | 1 | Q1a | |
| III-9 | F | H |  | 1 | Q1a | |
| III-10 | F | H | —CH=CH₂ | 1 | Q1a | |
| III-11 | Cl | H | Me | 1 | Q1a | |
| III-12 | Cl | H | Me | 2 | Q1a | |
| III-13 | Cl | H | Me | 1 | Q2 | |
| III-14 | Cl | H | Me | 1 | Q3a | |
| III-15 | Cl | H | Me | 1 | Q5a | |
| III-16 | Cl | H | Me | 1 | Q6a | |
| III-17 | Cl | H | Et | 1 | Q1a | |
| III-18 | Cl | H |  | 1 | Q1a | |
| III-19 | Cl | H | —CH=CH₂ | 1 | Q1a | |
| III-20 | Br | H | Me | 1 | Q1a | |
| III-21 | Br | H | Me | 1 | Q2 | |
| III-22 | Br | H | Me | 1 | Q3a | |
| III-23 | Br | H | Me | 1 | Q5a | |
| III-24 | Br | H | Me | 1 | Q7 | |
| III-25 | Br | H | Et | 1 | Q1 | |
| III-26 | Br | H |  | 1 | Q1a | |
| III-27 | Br | H | —CH=CH₂ | 1 | Q1a | |
| III-28 | I | H | Me | 1 | Q1a | |
| III-29 | I | H | Me | 1 | Q2 | |
| III-30 | I | H | Me | 1 | Q3a | |
| III-31 | I | H | Me | 1 | Q5a | |
| III-32 | I | H | Me | 1 | Q6a | |
| III-33 | I | H | Et | 1 | Q1a | |
| III-34 | I | H |  | 1 | Q1a | |
| III-35 | I | H | —CH=CH₂ | 1 | Q1a | |
| III-36 | CF₃ | H | Me | 1 | Q1a | |
| III-37 | CF₃ | H | Me | 1 | Q2 | |
| III-38 | CF₃ | H | Me | 1 | Q3a | |
| III-39 | CF₃ | H | Me | 1 | Q5a | |
| III-40 | CF₃ | H | Me | 1 | Q6a | |
| III-41 | CF₃ | H | Et | 1 | Q1a | |
| III-42 | CF₃ | H |  | 1 | Q1a | |
| III-43 | CF₃ | H | —CH=CH₂ | 1 | Q1a | |
| III-44 | OMe | H | Me | 1 | Q1a | |
| III-45 | OMe | H | Me | 1 | Q2 | |
| III-46 | OMe | H | Me | 1 | Q3a | |
| III-47 | OMe | H | Me | 1 | Q5a | |
| III-48 | OMe | H | Et | 1 | Q1a | |

TABLE 3-continued

| Compound No. | X | Y | R | n | Q | melting point (mp) or $n_D^{20}$ |
|---|---|---|---|---|---|---|
| III-49 | OMe | H | cyclopropyl | 1 | Q1a | |
| III-50 | OMe | H | —CH=CH$_2$ | 1 | Q1a | |
| III-51 | OSO$_2$Me | H | Me | 1 | Q1a | |
| III-52 | OSO$_2$Me | H | Me | 1 | Q2 | |
| III-53 | OSO$_2$Me | H | Me | 1 | Q3a | |
| III-54 | OSO$_2$Me | H | Me | 1 | Q5a | |
| III-55 | OSO$_2$Me | H | Et | 1 | Q1a | |
| III-56 | OSO$_2$Me | H | cyclopropyl | 1 | Q1a | |
| III-57 | OSO$_2$Me | H | —CH=CH$_2$ | 1 | Q1a | |
| III-58 | SMe | H | Me | 1 | Q1a | |
| III-59 | SMe | H | Me | 1 | Q | |
| III-60 | SMe | H | Me | 1 | Q3a | |
| III-61 | SMe | H | Et | 1 | Q1a | |
| III-62 | SMe | H | cyclopropyl | 1 | Q1a | |
| III-63 | SMe | H | —CH=CH$_2$ | 1 | Q1a | |
| III-64 | OSO$_2$Me | H | Me | 1 | Q1a | |
| III-65 | OSO$_2$Me | H | Me | 1 | Q2 | |
| III-66 | OSO$_2$Me | H | Me | 1 | Q3a | |
| III-67 | OSO$_2$Me | H | Me | 1 | Q5a | |
| III-68 | OSO$_2$Me | H | Et | 1 | Q1a | |
| III-69 | OSO$_2$Me | H | cyclopropyl | 1 | Q1a | |
| III-70 | OSO$_2$Me | H | —CH=CH$_2$ | 1 | Q1a | |
| III-71 | NO$_2$ | H | Me | 1 | Q1a | 82–87 |
| III-72 | NO$_2$ | H | Me | 2 | Q1a | |
| III-73 | NO$_2$ | H | Me | 1 | Q1b | |
| III-74 | NO$_2$ | H | Me | 1 | Q1c | |
| III-75 | NO$_2$ | H | Me | 1 | Q2 | |
| III-76 | NO$_2$ | H | Me | 1 | Q3a | |
| III-77 | NO$_2$ | H | Me | 1 | Q4a | |
| III-78 | NO$_2$ | H | Me | 1 | Q4b | |
| III-79 | NO$_2$ | H | Me | 1 | Q5a | |
| III-80 | NO$_2$ | H | Me | 1 | Q6a | |
| III-81 | NO$_2$ | H | Me | 1 | Q7 | |
| III-82 | NO$_2$ | H | Et | 1 | Q1a | |
| III-83 | NO$_2$ | H | Et | 1 | Q2 | |
| III-84 | NO$_2$ | H | Et | 1 | Q3a | |
| III-85 | NO$_2$ | H | Et | 1 | Q5a | |
| III-86 | NO$_2$ | H | Et | 1 | Q6a | |
| III-87 | NO$_2$ | H | n-Pr | 1 | Q1a | |
| III-88 | NO$_2$ | H | n-Pr | 1 | Q2 | |
| III-89 | NO$_2$ | H | i-Pr | 1 | Q1a | |
| III-90 | NO$_2$ | H | i-Pr | 1 | Q2 | |
| III-91 | NO$_2$ | H | cyclopropyl | 1 | Q1a | |
| III-92 | NO$_2$ | H | cyclopropyl | 1 | Q2 | |
| III-93 | NO$_2$ | H | cyclopropyl | 1 | Q3 | |
| III-94 | NO$_2$ | H | cyclopropyl | 1 | Q5a | |
| III-95 | NO$_2$ | H | cyclohexyl | 1 | Q1a | |
| III-96 | NO$_2$ | H | —CH=CH$_2$ | 1 | Q1a | |
| III-97 | NO$_2$ | H | —CH=CH$_2$ | 1 | Q2 | |
| III-98 | NO$_2$ | H | —CH=CH$_2$ | 1 | Q3a | |
| III-99 | NO$_2$ | H | —CH=CH$_2$ | 1 | Q5a | |
| III-100 | NO$_2$ | H | —CH$_2$CH=CH$_2$ | 1 | Q1a | |
| III-101 | NO$_2$ | H | Ph | 1 | Q1a | |
| III-102 | NO$_2$ | H | 2-Cl—Ph | 1 | Q1a | |
| III-103 | NO$_2$ | H | CH$_2$CH$_2$F | 1 | Q1a | |
| III-104 | NO$_2$ | H | CH$_2$CH$_2$Cl | 1 | Q1a | |
| III-105 | NO$_2$ | H | CH$_2$CF$_3$ | 1 | Q1a | |
| III-106 | NO$_2$ | H | CH$_2$CH$_2$F | 1 | Q1a | |
| III-107 | NO$_2$ | H | CH$_2$CF$_2$CF$_3$ | 1 | Q1a | |
| III-108 | NO$_2$ | H | CH$_2$CH$_2$CH$_2$F | 1 | Q1a | |
| III-109 | CN | H | Me | 1 | Q1a | |
| III-110 | CN | H | Me | 1 | Q2 | |
| III-111 | CN | H | Me | 1 | Q3a | |
| III-112 | CN | H | Me | 1 | Q5a | |
| III-113 | CN | H | Et | 1 | Q1a | |
| III-114 | CN | H | cyclopropyl | 1 | Q1a | |
| III-115 | CN | H | —CH=CH$_2$ | 1 | Q1a | |

SYNTHESIS EXAMPLE 4

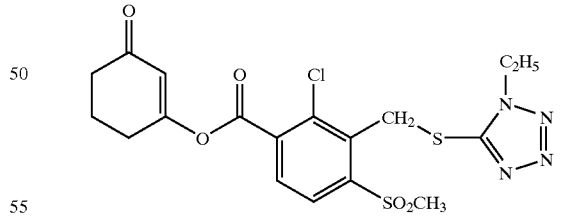

2-Chloro-3-{[(1-ethyl-1H-tetrazol-5-yl)thio]methyl}-4-methylsulfonyl-benzoic acid (0.77 g) and thionyl chloride (0.49 g) were added to 1,2-dichloroethane (30 ml) and the mixture was, after addition of 2 drops of N,N-dimethylformamide, refluxed for 3 hours. After cooling, the residue obtained by distilling off the solvent was dissolved in dichloromethane (10 ml) and the mixture was added dropwise to a solution of 1,3-cyclohexanedione (0.28 g) and triethylamine (0.28 g) in dichloromethane (10 ml) at 5° C.

and stirred at room temperature for 6 hours. After the reaction the mixture was extracted with dichloromethane (100 ml), washed with diluted hydrochloric acid and an aqueous dolution of sodium hydrogen carbonate, and dried with anhydrous magnesium sulfate. The residue obtained by distilling off the dichloromethane was purified by silica gel column chromatography (eluant:ethyl acetate:hexane=3:7) to obtain the objective 3-oxo-1-cyclohexenyl 2-chloro-3-{[(1-ethyl-1H-tetrazol-5-yl)thio]methyl}-4-methylsulfonylbenzoate (0.83 g). mp: 12214 123° C.

SYNTHESIS EXAMPLE 5

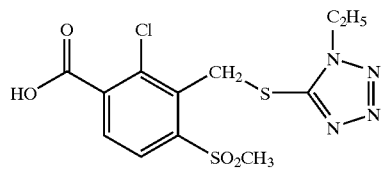

To a solution of methyl 2-chloro-3-{[(1-ethyl-1H-tetrazol-5-yl)thio]methyl}-4-meth-ylsulfonylbenzoate (0.83 g) in dioxane (15 ml), a 10N aqueous solution of sodium hydroxide (1.0 ml) and water (2 ml) were added and the mixture was stirred at room temperature for 3 hours. Water (30 ml) is added. Then, after concentration under reduced pressure, a 10N aqueous solution of sodium hydroxide (1.0 ml) was added to the concentrate and the concentrate is washed with ethyl acetate (100 ml). The aqueous layer was acidified with hydrochloric acid and extracted with ethyl acetate. The organic layer was washed with saturated aqueous solution of sodium chloride and dried with anhydrous magnesium sulfate. Ethyl acetate was distilled off to obtain the objected 2-chloro-3-{[(1-ethyl-1H-tetrazol-5-yl)thio]methyl}-4-methyl-sulfonylbenzoic acid (0.80 g). mp: 193-195° C.

SYNTHESIS EXAMPLE 6

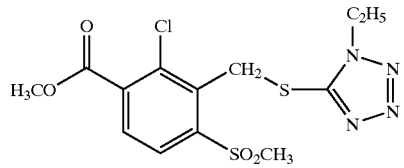

1-Ethyl-5-mercaptotetrazole (0.31 g) and methyl 3-bromomethyl-2-chloro-4-methyl-sulfonylbenzoate (0.80 g) were suspended in acetonitrile (20 ml) and the suspension was, after addition of potassium carbonate (0.32 g), refluxed for 3 hours. After addition of cold water upon the completion of the reaction, the mixture was extracted with ethyl acetate (100 ml) and dried with anhydrous magnesium sulfate. The residue obtained by distilling off the ethyl acetate was recrystallized from dichloromethane-hexane to obtain the objected methyl 2-chloro-3-{[(1-ethyl-1H-tetrazol-5-yl)thio]methyl}-4-methylsulfonyl-benzoate (0.88 g). Mp: 109–110° C.

TEST EXAMPLE 1

Test for Herbicidal Effect Against Paddy Field Weeds

Preparation of a Formulation of the Active Compound

| Carrier | Acetone 5 parts by weight |
|---|---|
| Emulsifier | Benzyloxypolyglycolether 1 part by weight |

A formulation of the active substance is obtained as an emulsion by mixing 1 part by weight of the active compound with the above-mentioned amount of carrier and emulsifier. A prescribed amount of the formulation is diluted with water.

Test Method

In a greenhouse 3 seedlings of paddy rice (cultivar: Nipponbare) of 2.5 leafstage (15 cm tall) were planted in a 500 cm² pot filled with paddy field soil. Then seeds or tubers of smallflower, bulrush, monochoria, broad-leaved weeds (common false pimpernel, Indian toothcup, long stemmed water wort, Dopatriun junceum Hammilt etc.) and Japanese ribbon wapato were inoculated and water was poured to a depth of about 2–3 cm.

5 Days after the rice transplantation a formulation of each active compound prepared according to the aforementioned preparation method was applied to the surface of the water. The herbicidal effect was examined after 3 weeks from the treatment during which period the water depth of 3 cm was maintained. The herbicidal effect was rated as 100% in the case of complete extiinction and as 0% in the case of no herbicidal effect.

As a result, the compounds No. II-18, II-117, II-122, II-131, II-194, II-212 and III-71 showed at the application rate of 0.25 kg/ha a herbicidal effect of more than 90% against paddy field weeds and showed safety to the transplanted paddy rice.

TEST EXAMPLE 2

Test of Pre-emergence Soil Treatment Against Field Weeds

Test Method

In a greenhouse, on the surface layer of a 120 cm² pot filled with field soil, and then seeds of barnyardgrass, foxtail, common amaranth and knotweed were sown and covered with soil. The prescribed amount of chemicals prepared in the same manner as in the above-mentioned Test Example 1 was spread uniformly on the soil surface layer of each test pot. The herbicidal effect was examined after 4 weeks from the treatment.

Effects:

The compounds No. II-117, II-122 and II-194 showed at application rate of 2.0 kg/ha herbicidal activities of more than 90% against objective weeds (barnyardgrass, foxtail, common amaranth and knotweed).

TEST EXAMPLE 3

Test of Post-emergence Foliage Treatment Against Field Weeds

Test Method

In a greenhouse, seeds of barnyardgrass, foxtail, common amaranth and knotweed were sown in 120 cm² pots filled with field soil and covered with soil. After 10 days after the sowing and soil covering (weeds were 2-leafstage in average) the prescribed amount of chemicals prepared in the same manner as in the above-mentioned Test Example 1 was spread uniformly on the foliage of the test plants in each test pot. The herbicidal effect was examined after 3 weeks from the treatment.

Results:

The compounds No. II-18, II-117, II-122, II-131, II-194, II-212 and II-276 showed at the chemical amount of 2.0 kg/ha herbicidal activities of more than 90% against barnyardgrass, foxtail, common amaranth and knotweed.

TEST EXAMPLE 4

Test for Synergistic Action by Foliar Spray Application

Preparation of the Test Solution

| Carrier | acetone, 5 parts by weight |
|---|---|
| Emulsifier | benzyloxypolyglycol ether, 1 parts by weight |

One part of an active compound and the above amounts of carrier and emulsifier are mixed to obtain a formulation of the active substance as an emulsion. A prescribed amount of this formulation is diluted with water to prepare testing solutions.

Test Method

In a greenhouse, paddy soil was filled in pots (250 cm²), and seeds of weed (barnyardgrass, bulrush, monochoria and falsepimpemel) were inoculated in the surface layer of the soil in the pots under wet conditions and covered with soil. All of the weed species were individually inoculated in each pot. Each pot was watered to 2 cm in depth. When the weeds grew up to 1.514 2.2 leaf stage (or pair), a predetermined amount of the compound as a testing solution prepared in the above was applied to the weeds in pots by foliar spray after draining the water in the pot. On the day following the application, the pots were irrigated again to 2 cm of water depth. The herbicidal effect was evaluated at 4 weeks after the application on a scale of 0 (not active) to 100 (complete damage).

Test results of test example 4 are shown in Table 4.

TEST EXAMPLE 5

Test for Synergistic Action by Water Surefice Application

Test Method

In a greenhouse, paddy soil was filled in pots (250 cm²), and seeds of weed (barnyardgrass, bulrush, monochoria, falsepimpemel, indian toothcup, waterwort and flatstage) were inoculated in the surface layer of the soil in the pots under wet conditions and covered with soil. All of the weed species were individually inoculated in each pot. Each pot was watered to 2 cm in depth and the depth was kept during the test period. When the weeds grew up to 1.5–2.2 leaf stage (or pair), a predetermined amount of the compound as a testing solution prepared in the same manner as the above-mentioned Test Example 4 was applied to the pots by water surface treatment method. The herbicidal effect was evaluated at 4 weeks after the application on the same scale as in thetest method of Test Example 4.

Test results of test example 5 are shown in Table 5.

Synergistic action of Test Example 4 and Test Example 5 were evaluated by Colby's equation.

$$Colby: E = X + \left[Y \times \frac{(100 - X)}{100}\right]$$

E: expected herbicidal activity at p+q g/ha

X: the percentage of herbicidal activity at p g/ha

Y: the percentage of herbicidal activity at q g/ha

The following abbreviations are used in Table 4 and Table 5:

| CYPSE | represents *Cyperus serotinus* (flatstage), |
|---|---|
| ECHSS | represents Echinochloa spp. (barnyardgrass), |
| ELTTP | reprerstnts *Elatine triandra* (waterwort), |
| LIDPY | represents *Lindernia pyridaria* (flasepimpernel), |
| MOOVP | represents *Monochoria vaginalis* (monochoria), |
| ROTIN | represents *Rotala indica* (indian toothcup), |

Compounds (1) in Table 4 and Table 5 are listed by the compound numbers previously used in Tables 1, 2 and 3.

In Table 4 and Table 5 other known herbicides are represented by the capital letters as shown in the following list:

| A | 4-(2-chlorophenyl)-N-cyclohexyl-N-ethyl-4,5-dihydro-5-oxo-1H-tetrazole-1-carboxamide (fentrazamide), |
|---|---|
| B | 3,'4'-dichloropropionanilide (propanil), |
| C | N,N-diethyl-3-mesitylsulfonyl-1H-1,2,4-triazole-1-carboxamide (cafenstrole), |
| D | 3-[1-(3,5-dichlorophenyl)-1-methylethyl]-2,3-dihydro-6-methyl-5-phenyl-4H-1,3-oxazin-4-one (oxaziclomefone), |
| E | 2-chloro-2',6'-diethyl-N-(2-propoxyethyl) acetamide (pretilachlor), |
| F | 2-(1,3-benzothiazol-2-yloxy)-N-methylacetanilide (mefenacet), |
| G | (RS)-2-[2-(3-chlorophenyl)2,3-epoxypropyl]-2-ethylindan-1,3-dione (indanofan). |

TABLE 4

Herbicidal efficacy (%) by foliar spray application

| | Herbicidal efficacy (%) | | | |
|---|---|---|---|---|
| Test plant | compound (1) (g a.i./ha) | known herbicide (g a.i./ha) | compound (1) + known herbicide (g a.i./ha) | Expected activity E according to Colby (%) |
| 1st run: | II-131 (125) | A (135) | II-131 + A (125 + 135) | II-131 + A |
| SCPSS | 70 | 60 | 90 | 88 |
| MOOVP | 70 | 60 | 95 | 88 |
| LIDPY | 50 | 50 | 80 | 75 |
| 2nd run: | II-131 (125) | B (750) | II-131 + B (125 + 750) | II-131 + B |
| ECHSS | 40 | 30 | 80 | 58 |
| SCPSS | 70 | 10 | 80 | 73 |
| MOOVP | 70 | 30 | 90 | 79 |
| LIDPY | 50 | 40 | 80 | 70 |

TABLE 5

Herbicidal efficacy (%) by water surface application

| Test plant | compound (1) (g a.i./ha) | known herbicide (g a.i./ha) | compound (1) + known herbicide (g a.i./ha) | Expected activity E according to Colby (%) |
|---|---|---|---|---|
| 1st run: | II-117 (75) | A (100) | II-117 + A (75 + 100) | II-117 + A |
| LIDPY | 75 | 50 | 100 | 87.5 |
| ROTIN | 50 | 70 | 95 | 85 |
| ELTTP | 50 | 80 | 95 | 90 |
| 2nd run: | II-117 (75) | C (100) | II-117 + C (75 + 100) | II-117 + C |
| LIDPY | 70 | 60 | 90 | 88 |
| 3rd run: | II-122 (60) | D (40) | II-122 + D (60 + 40) | II-122 + D |
| ECHSS | 0 | 80 | 85 | 80 |
| SCPSS | 60 | 30 | 80 | 72 |
| LIDPY | 70 | 40 | 90 | 82 |
| 4th run: | II-18 (60) | E (300) | II-18 + E (60 + 300) | II-18 + E |
| MOOVP | 80 | 60 | 100 | 92 |
| LIDPY | 60 | 60 | 95 | 84 |
| CYPSE | 50 | 40 | 80 | 70 |
| 5th run: | III-71 (125) | F (500) | III-71 + F (125 + 500) | III-71 + F |
| LIDPY | 80 | 40 | 95 | 88 |
| ROTIN | 70 | 40 | 90 | 82 |
| run6: | III-71 (125) | G (75) | III-71 + G (125 + 75) | III-71 + G |
| LIDPY | 80 | 60 | 98 | 92 |
| ROTIN | 70 | 60 | 95 | 88 |

TEST EXAMPLE 6

Test for Safening Action on Rice by Water Surface Application

Test Method

In a greenhouse, paddy soil was filled in pots (1,000 cm$^2$), and seeds of rice (cv. Nipponbare) were sown in the surface layer of the soil in the pots under wet conditions. 7 days after seeding, at the one leaf stage of the rice seedlings, the pots were watered to 3 cm in depth and the depth was kept during the test period. When the rice seedlings grew up to 1.5 leaf stage during the 9 days after seeding, a predetermined amount of the compound as a testing solution prepared in the same manner as the above-mentioned Test Example 4 was applied to the pots by water surface treatment method. The phytotoxicity to rice seedlings was evaluated at 3 weeks after the application on a scale of 0 (no damage) to 100 (complete deth).

Test result of test example 6 are shown in Table 6.

Safening action of Test Example 6 were evaluated by Colby's equation.

$$Colby: E = X + \left[ Y \times \frac{(100 - X)}{100} \right]$$

E: expected phytotoxicity at p+q g/ha
X: expected phytotoxicity at p g/ha
Y: expected phytotoxicity at q g/ha Compounds (1) in Table 6 are listed by by the compound numbers previously uesd in Tables 1, 2 and 3.

In Table 6 the known safeners are represented by the capital letters as shown in the following list:

a   N,N-diallyl-2,2-dichloroacetamide (dichlormid),
b   4,6-dichloro-2-phenylpyrimidine (fenclorin),
c   diethyl (RS)-1-(2,4-dichlorophenyl)-5-methyl-2-pyrazoline-3,5-dicarboxylate (mefenpyr-diethyl),
d   N-(4-methylphenyl)-N'-(1-methyl-1-phenylethyl)urea (dymron),
e   2-(dichloroacetyl)-2,2,5-trimethyl-oxazolidine (R-29148),
f   1H,3H-naphtho [1,8-cd] pyran-1,3-dione (naphthalic anhydride).

TABLE 6

Safening efficacy (%) by water surface application

| compound (1) (g a.i./ha) | Phyto-toxicity (%) | safener (g a.i./ha) | phyto-toxicity (%) | compound (1) + safener (g a.i./ha) | phyto-toxicity (%) | Expected phytotoxicity (E) according to Colby (%) |
|---|---|---|---|---|---|---|
| II-276 (400) | 40 | a (200) | 0 | II-276 + a (400 + 200) | 5 | 40 |
| | | b (400) | 0 | II-276 + b (400 + 400) | 20 | 40 |
| | | c (400) | 20 | II-276 + c (400 + 400) | 25 | 52 |
| II-131 (400) | 40 | d (400) | 0 | II-131 + d (400 + 400) | 10 | 40 |
| | | b (400) | 0 | II-131 + b (400 + 200) | 15 | 40 |
| | | e (200) | 0 | II-131 + e (400 + 200) | 20 | 40 |
| II-122 (600) | 30 | d (400) | 0 | II-122 + d (600 + 400) | 10 | 30 |
| | | a (200) | 0 | II-122 + a (600 + 200) | 10 | 30 |
| | | b (400) | 0 | II-122 + b (600 + 400) | 5 | 30 |
| | | f (400) | 0 | II-122 + f (600 + 400) | 0 | 30 |
| II-117 (400) | 60 | d (400) | 0 | II-117 + d (400 + 400) | 30 | 60 |
| | | a (200) | 0 | II-117 + a (400 + 200) | 40 | 60 |
| | | f (400) | 0 | II-117 + f (400 + 400) | 30 | 60 |
| III-71 (600) | 30 | a (200) | 0 | III-71 + a (600 + 200) | 10 | 30 |
| | | c (400) | 20 | III-71 + c (600 + 400) | 20 | 44 |
| II-194 (400) | 50 | d (400) | 0 | II-194 + d (400 + 400) | 25 | 50 |
| | | b (400) | 0 | II-194 + b (400 + 400) | 30 | 50 |
| | | f (400) | 0 | II-194 + f (400 + 400) | 20 | 50 |

Formulation Example 1 (Granule)

To a mixture of the compound No. II-18 of the present invention (2.5 parts), bentonite (montrnorillonite) (30 parts), talc (65.5 parts) and ligninsulphonate salt (2 parts), water (25 parts) is added. The mixture is well kneaded, made in granules of 10–40 mesh by an extrusion granulator and dried at 40–50° C. to obtain a granule.

Formulation Example 2 (Granule)

Clay mineral particles having particle size distribution of 0.2–2 mm (95 parts) are put in a rotary mixer. While rotating it, the compound No. II-117 of the present invention (5 parts) is sprayed together with a liquid diluent into the mixer wetted uniformly and dried at 40–50° C. to obtain granules.

Formulation Example 3 (Emulsifiable Concentrate)

The compound No. II-122 of the present invention (30 parts), xylene (5 parts), poly-oxyethylenealkyl phenyl ether (8 parts) and calcium alkylbenzenesulfonate (7 parts) are mixed and stirred to obtain an emulsion.

Formulation Example 4 (Wettable Powder)

The compound No. II-194 of the present invention (15 parts), a mixture of white carbon (hydrous amorphous silicon oxide fine powders) and powder clay (1:5) (80 parts), sodium alkylbenzenesulfonate (2 parts) and sodium alkylnaphthalene-sulfonate-formalin-polymer (3 parts) are mixed in powder form and made into a wettable powder.

Formulation Example 5 (Water-dispersible Granule)

The compound No. II-18 of the present invention (20 parts), sodium ligninsulfonate (30 parts), bentonite (15 parts) and calcined diatomaceous earth powder (35 parts) are well mixed, added with water, extruded using a 0.3 mm screen and dried to obtain a water-dispersible granules.

What is claimed is:
1. A compound of the formula (I)

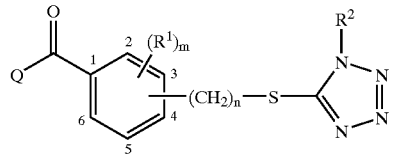

wherein $R^1$ represents halogen, methyl, ethyl, halomethyl, methoxy, ethoxy, $C_{1-2}$ haloalkoxy, methylthio, ethylthio, $C_{1-3}$ alkylsulfonyl, methyl sulfonyloxy, ethylsulfonyloxy, nitro or cyano, $R^2$ represents $C_{1-6}$ alkyl, $C_{3-6}$ cycloalkyl which may be optionally substituted with halogen or $C_{1-3}$ alkyl, $C_{1-4}$ haloalkyl, $C_{2-6}$ alkenyl, or phenyl which may be optionally substituted with halogen, $C_{1-3}$ alkyl, $C_{1-2}$ haloalkyl or nitro, m represents 0, 1 or 2, the two $R^1$ substituents may be identical or different, in case m represents 2, n represents 1 or 2, Q represents one of the following groups

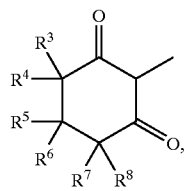
(Q-1)

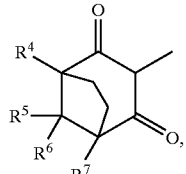
(Q-2)

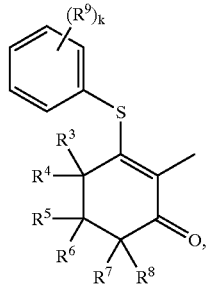
(Q-3)

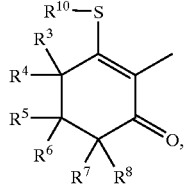
(Q-4)

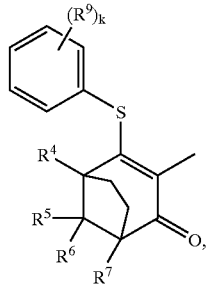
(Q-5)

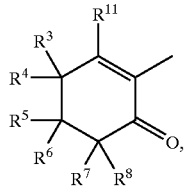
(Q-6)

or

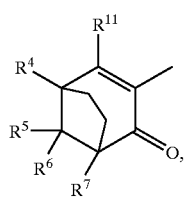
(Q-7)

wherein
$R^3$, $R^4$, $R^5$, $R^6$, $R^7$ and $R^8$ are identical or different and each represents a hydrogen atom or methyl,
$R^9$ represents a hydrogen atom, halogen, $C_{1-3}$ alkyl, halomethyl, methoxy or nitro,
$R^{10}$ represents $C_{1-6}$ alkyl,
$R^{11}$ represents halogen, and
k represents 1 or 2.

2. A compound of the formula (I) according to claim 1 wherein $R^1$ represents fluoro, chloro, bromo, methyl, ethyl, trifluoromethyl, methoxy, ethoxy, $C_{1-2}$ haloalkoxy, methylthio, ethylthio, methyl sulfonyl, ethylsulfonyl, methylsulfonyloxy, ethylsulfonyloxy, nitro or cyano, $R^2$ represents $C_{1-3}$ alkyl, cyclopropyl which may be optonally substituted with fluoro, chloro, methyl or ethyl, $C_{1-3}$ haloalkyl, $C_{2-4}$ alkenyl, or phenyl which may be optionally substituted with fluoro, chloro, methyl, ethyl, trifluoromenthyl or nitro, m represents 1 or 2 the two $R^1$ substituents may be identical or different, in case m represents 2, n represents 1 or 2, Q represents one of the following groups

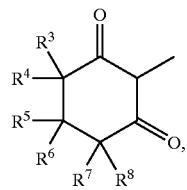
(Q-1)

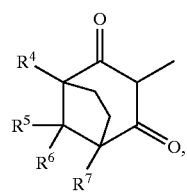
(Q-2)

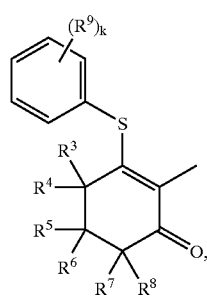
(Q-3)

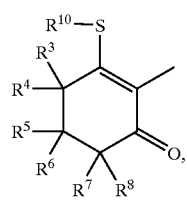
(Q-4)

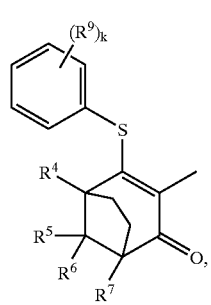
(Q-5)

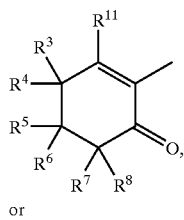
(Q-6)

or

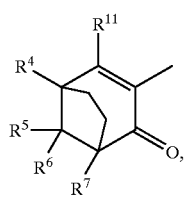
(Q-7)

wherein $R^3$, $R^4$, $R^5$, $R^6$, $R^7$ and $R^8$ are identical or different and each represents a hydrogen atom or methyl $R^9$ represents a hydrogen atom, fluoro, chloro, methyl, ethyl or trifluoro methyl $R^{10}$ represents methyl or ethyl, $R^{11}$ represents chloro or bromo, and k represents 1.

3. The compound of the formula (I) according to claim 1 wherein $R^1$ represents chloro, bromo, methyl or methylsulfonyl, $R^2$ represents methyl, ethyl, n-propyl, isopropyl or cyclopropyl, m represents 2, and in this case the two $R^1$ substituents are bond respectively to the 2-position and 4-position of a benzene ring and the two $R^1$ substituents may be identical or different, n represents 1, the group

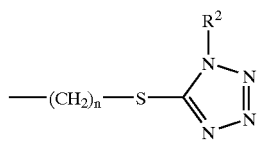

bonds to the 3-position of the benzene ring, and

Q represents one of the following groups

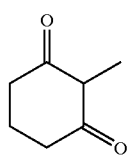

or

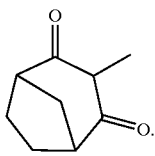

4. A process for the preparation of the compound of claim 1 comprising
a) in case of preparing a compound of the formula (I) wherein Q represents groups (Q-1) or (Q-2):
reacting a compound of the formula (II)

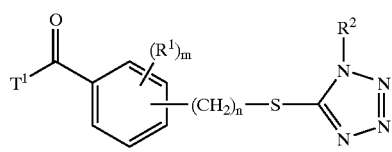

(II)

wherein
$R^1$, $R^2$, m and n have the same definition as in claim 1, and
$T^1$ represents one of the following groups

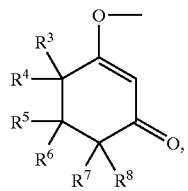

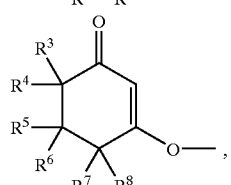

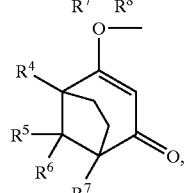

or

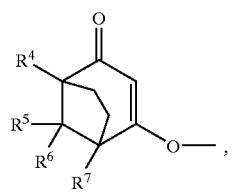

wherein
$R^3$, $R^4$, $R^5$, $R^6$, $R^7$ and $R^8$ have the same definition as in claim 1,
to a rearrangement in the presence of inert solvents, and optionally, in the presence of a base and cyanide, and optionally, in the presence of a phase-transfer catalyst,
or
b) in case of preparing a compound of the formula (I) wherein Q represents groups (Q-6) or (Q-7) and $R^{11}$ in said groups represents chloro or bromo:

reacting a compound of the formula (Ib)

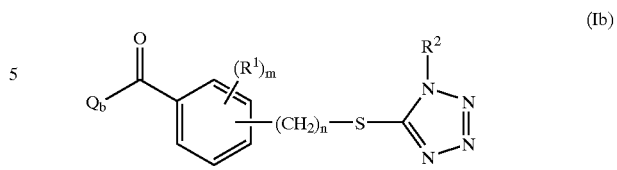

(Ib)

wherein
$R^1$, $R^2$, m and n have the same definition as in claim 1, and
$Q_b$ represents one of the following groups

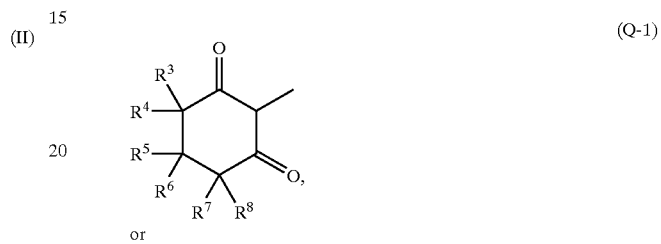

(Q-1)

or

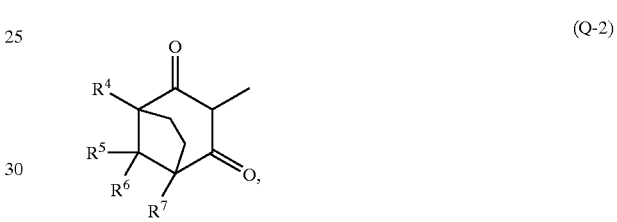

(Q-2)

wherein
$R^3$, $R^4$, $R^5$, $R^6$, $R^7$ and $R^8$ have the same definition as in claim 1,
with a halogenating agent in the presence of one or more inert solvents,
or
c) in case of preparing a compound of the formula (I) wherein Q represents groups (Q-3), (Q4) or (Q-5):
reacting a compound of the formula (Ic)

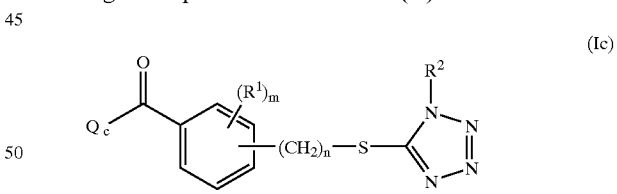

(Ic)

wherein
$R^1$, $R^2$, m and n have the same definition as in claim 1, and
$Q_c$ represents one of the following groups

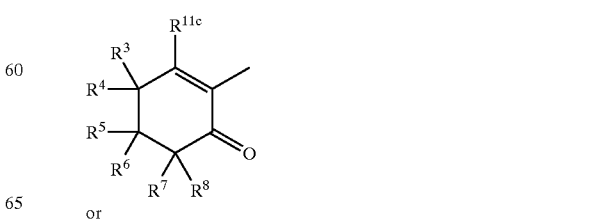

or

-continued

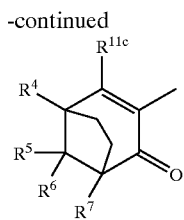

wherein

R³, R⁴, R⁵, R⁶, R⁷ and R⁸ have the same definition as in claim 1,

R$^{11c}$ represents chloro or bromo, with a compound of the formula (III)

$$R^{12}-SH \qquad (III)$$

wherein

R¹² represents the group

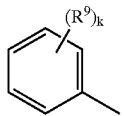

or

R¹⁰ wherein

R⁹, R¹⁰ and k have the same definition as in claim 1, in the presence of one or more inert solvents, and optionally, in the presence of an acid binding agent.

5. A herbicidal composition comprising at least one compound according to claim 1.

6. A method for combating weeds comprising allowing a compound according to claim 1 to act on weeds and/or their habitat.

7. A process for the preparation of a herbicidal composition, comprising mixing a compound according to claim 1 with one or more extenders and/or surface active agents.

8. A compound represented by the formula (X)

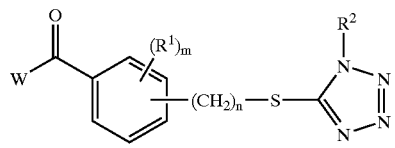

wherein

R¹, R², m and n have the same definition as in claim 1,

W represents halogen, hydroxy, $C_{1-4}$ alkoxy or one of the following groups

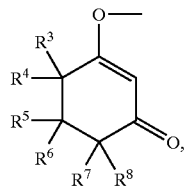

-continued

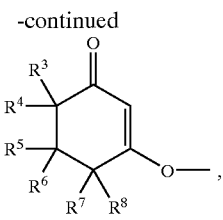

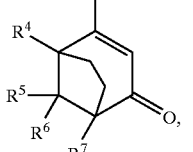

or

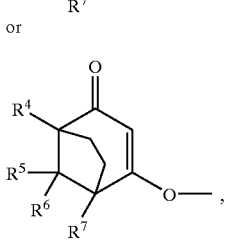

wherein

R³, R⁴, R⁵, R⁶, R⁷ and R⁸ have the same definition as in claim 1.

9. A herbicidal composition containing an active substance combination, said active substance combination comprising a tetrazole derivative of the formula (I) according to claim 1 and at least one known active ingredient selected from the group consisting of acetamide herbicides, amide herbicides, benzofuran herbicides, indanedione herbicides, pyrazole herbicides, oxazinone herbicides, sulfonylurea herbicides, thiocarbamate herbicides, triazine herbicides, triazole herbicides, quinoline herbicides, isoxazole herbicides, dithiophosphate herbicides, oxyacetamide herbicides, tetrazolinone herbicides, dicarboxyimide herbicides, trione herbicides, phenoxypropinate herbicides, benzoic acid herbicides, diphenylether herbicides, pyridinedicarbothioate herbicides, phenoxy herbicides, urea herbicides, naphthalenedione herbicides and isoxazolidinone herbicides.

10. A herbicidal composition containing an active substance combination, said active substance combination comprising a tetrazole derivative of formula (I) according to claim 1 and a safener.

11. A herbicidal composition containing an active substance combination, said active substance combination comprising a tetrazole derivative of the formula (I) according to claim 1 together with at least one active ingredient selected from the group consisting of acetamide herbicides, amide herbicides, benzofuran herbicides, indanedione herbicides, pyrazole herbicides, oxazinone herbicides, sulfonylurea herbicides, thiocarbamate herbicides, triazine herbicides, triazole herbicides, quinoline herbicides, isoxazole herbicides, dithiophosphate herbicides, oxyacetamide herbicides, tetrazolinone herbicides, dicarboxyimide herbicides, trione herbicides, phenoxypropinate herbicides, benzoic acid herbicides, diphenylether herbicides, pyridinedicarbothioate herbicides, phenoxy herbicides, urea herbicides, naphthalenedione herbicides and isoxazolidinone herbicides, and a safener.

12. A process for combating weeds comprising allowing an active substance combination according to claim 9 to act on the weeds and/or their habitat.

13. A process for the preparation of a herbicidal composition, comprising mixing an active substance combination according to claim 9 with one or more extenders and/or surface-active agents.

14. A composition according to claim 10 wherein the safener is selected from the group consisting of 4-dichloroacetyl-1-oxa-4-aza-spiro[4.5]-decane (AD-67), 1-dichloroacetyl-hexahydro-3,3,8a-trimethylpyrrolo[1,2-a]-pyrimidin-6(2H)-one (dicyclonon, BAS-145138), 4-dichloroacetyl-3,4-dihydro-3-methyl-2H-1,4-benzoxazine (benoxacor), 1-methyl-hexyl 5-chloro-quinolin-8-oxy-acetate (cloquintocet-mexyl), α-(cyanomethoximino)-phenylacetonitrile (cyometrinil), 2,4-dichloro-phenoxy acetic acid (2,4-D), 2,2-dichloro-N-(2-oxo-2-(2-propenylamino)-ethyl)-N-(2-propenyl)-acetamide (DKA-24), 2,2-dichloro-N,N-di-2-propenyl acetamide (dichlormid), 1-(1-methyl-1-phenyl-ethyl)-3-(4-methyl-phenyl)-urea (daimuron, dymron), 4,6-dichloro-2-phenyl-pyrimidine (fenclorim), ethyl 1-(2,4-dichloro-phenyl)-5-trichloro-methyl-1H-1,2,4-triazole-3-carboxylate (fenchlorazole-ethyl), phenyl-methyl 2-chloro-4-trifluoromethyl-thiazole-5-carboxylate (flurazole), 4-chloro-N-(1,3-dioxolan-2-yl-methoxy)-α-trifluoro-acetophenone oxime (fluxofenim), 3-dichloroacetyl-5-(2-furanyl)-2,2-dimethyl-oxazolidine (furilazole, MON-13900), ethyl-4,5-dihydro-5,5-diphenyl-3-isoxazolecarboxylate (isoxadifen-ethyl), diethyl-1-(2,4-dichloro-phenyl)-4,5-dihydro-5-methyl-1H-pyrazole-3,5-dicarboxylate (mefenpyr-diethyl), 2-dichloromethyl-2-methyl-1,3-dioxolane (MG-191), naphthalic anhydride, α-(1,3-dioxolan-2-yl-methoximino)-phenylacetonitrile (oxabetrinil), 2,2-dichloro-N-(1,3-dioxolan-2-yl-methyl)-N-(2-propenyl)-acetamide (PPG-1292), and 3-dichloroacetyl-2,2,5-trimethyl-oxazolidine (R-29148).

15. A composition according to claim 11 wherein the safener is selected from the group consisting of 4-dichloroacetyl-1-oxa-4-aza-spiro[4.5]-decane (AD-67), 1-dichloroacetyl-hexahydro-3,3,8a-trimethylpyrrolo[1,2-a]-pyrimidin-6(2H)-one (dicyclonon, BAS-145138), 4-dichloroacetyl-3,4-dihydro-3-methyl-2H-1,4-benzoxazine (benoxacor), 1-methyl-hexyl 5-chloro-quinolin-8-oxy-acetate (cloquintocet-mexyl), α-(cyanomethoximino)-phenylacetonitrile (cyometrinil), 2,4-dichloro-phenoxy acetic acid (2,4-D), 2,2-dichloro-N-(2-oxo-2-(2-propenylamino)-ethyl)-N-(2-propenyl)-acetamide (DKA-24), 2,2-dichloro-N,N-di-2-propenyl acetamide (dichlormid), 1-(1-methyl-1-phenyl-ethyl)-3-(4-methyl-phenyl)-urea (daimuron, dymron), 4,6-dichloro-2-phenyl-pyrimidine (fenclorim), ethyl 1-(2,4-dichloro-phenyl)-5-trichloro-methyl-1H-1,2,4-triazole-3-carboxylate (fenchlorazole-ethyl), phenyl-methyl 2-chloro-4-trifluoromethyl-thiazole-5-carboxylate (flurazole), 4-chloro-N-(1,3-dioxolan-2-yl-methoxy)-α-trifluoro-acetophenone oxime (fluxofenim), 3-dichloroacetyl-5-(2-furanyl)-2,2-dimethyl-oxazolidine (furilazole, MON-13900), ethyl-4,5-dihydro-5,5-diphenyl-3-isoxazolecarboxylate (isoxadifen-ethyl), diethyl-1-(2,4-dichloro-phenyl)-4,5-dihydro-5-methyl-1H-pyrazole-3,5-dicarboxylate (mefenpyr-diethyl), 2-dichloromethyl-2-methyl-1,3-dioxolane (MG-191), naphthalic anhydride, α-(1,3-dioxolan-2-yl-methoximino)-phenylacetonitrile (oxabetrinil), 2,2-dichloro-N-(1,3-dioxolan-2-yl-methyl)-N-(2-propenyl)-acetamide (PPG-1292), and 3-dichloroacetyl-2,2,5-trimethyl-oxazolidine (R-29148).

* * * * *